United States Patent
Benkovic et al.

(10) Patent No.: US 10,160,867 B2
(45) Date of Patent: Dec. 25, 2018

(54) BENZOXABOROLE-CONTAINING COATING RESISTANT TO CELLULOSE-SUPPORTABLE FUNGUS

(71) Applicants: Stephen J. Benkovic, State College, PA (US); Chunyu Liu, Philadelphia, PA (US); Edward Q. Kaiser, State College, PA (US)

(72) Inventors: Stephen J. Benkovic, State College, PA (US); Chunyu Liu, Philadelphia, PA (US); Edward Q. Kaiser, State College, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 0 days.

(21) Appl. No.: 15/227,154

(22) Filed: Aug. 3, 2016

(65) Prior Publication Data

US 2017/0037258 A1    Feb. 9, 2017

Related U.S. Application Data

(60) Provisional application No. 62/201,836, filed on Aug. 6, 2015.

(51) Int. Cl.

| | | |
|---|---|---|
| *A01N 55/08* | (2006.01) |
| *C07F 5/04* | (2006.01) |
| *C08K 5/55* | (2006.01) |
| *C09D 5/14* | (2006.01) |
| *C09D 5/02* | (2006.01) |
| *C09D 121/02* | (2006.01) |
| *C08K 5/00* | (2006.01) |

(52) U.S. Cl.
CPC ............ *C09D 5/14* (2013.01); *A01N 55/08* (2013.01); *C07F 5/04* (2013.01); *C09D 5/025* (2013.01); *C09D 121/02* (2013.01); *C08K 5/0058* (2013.01); *C08K 5/55* (2013.01)

(58) Field of Classification Search
None
See application file for complete search history.

(56) References Cited

U.S. PATENT DOCUMENTS

| | | | |
|---|---|---|---|
| 3,215,660 A | 11/1965 | Byram et al. | |
| 3,483,148 A | 12/1969 | Desmarais et al. | |
| 3,873,279 A * | 3/1975 | Singer | C02F 1/50 44/314 |

(Continued)

FOREIGN PATENT DOCUMENTS

GB          964186          7/1964

OTHER PUBLICATIONS

STIC structure search 15227154-558945—EICSEARCH (Year: 2018).*

(Continued)

*Primary Examiner* — Peter A Salamon
(74) *Attorney, Agent, or Firm* — Husch Blackwell LLP

(57) ABSTRACT

A latex paint composition that contains a film-forming binder and pigment dispersed in an aqueous vehicle and also contains an effective amount of one or more cellulose-supportable fungus growth-inhibiting benzoxaborole compounds of Formula C is disclosed. A method of using that latex paint to inhibit the growth of a cellulose-supportable fungus on a cellulosic surface is also disclosed, as is a method of inhibiting such growth by painting over an fungus-infected surface with a contemplated latex paint.

23 Claims, 1 Drawing Sheet

(56) References Cited

U.S. PATENT DOCUMENTS

| | | | |
|---|---|---|---|
| 4,069,186 A | 1/1978 | Ramig | |
| 4,277,385 A | 7/1981 | Carroll et al. | |
| 4,283,320 A | 8/1981 | Carroll et al. | |
| 4,800,107 A | 1/1989 | Wickert | |
| 5,880,188 A * | 3/1999 | Austin | A01N 55/08 424/405 |
| 7,482,395 B2 | 1/2009 | Maybey et al. | |
| 7,582,621 B2 * | 9/2009 | Baker | C07F 5/02 514/64 |
| 7,767,657 B2 * | 8/2010 | Baker | C07F 5/025 514/64 |
| 7,816,344 B2 * | 10/2010 | Baker | C07F 5/025 514/64 |
| 8,168,614 B2 * | 5/2012 | Baker | A61K 31/69 514/64 |
| 8,524,636 B2 * | 9/2013 | Sianawati | A01N 47/12 504/126 |
| 2005/0054644 A1 * | 3/2005 | Lee | C07F 5/025 514/242 |
| 2007/0265226 A1 * | 11/2007 | Lee | C07F 5/025 514/64 |
| 2012/0165191 A1 | 6/2012 | Sianawati et al. | |
| 2012/0289686 A1 * | 11/2012 | Baker | C07F 5/025 534/558 |
| 2014/0135259 A1 * | 5/2014 | Halfon | A61K 31/405 514/4.3 |
| 2014/0221312 A1 | 8/2014 | Maclean et al. | |
| 2014/0259230 A1 * | 9/2014 | Bobbio | A01N 55/08 800/298 |

OTHER PUBLICATIONS

Schumacher et al., *J. Molec Recognit* (Nov. 5, 2011) 24(6):953-959.
ISR—Written Opinion PCT/US2016/045329 (WO 2017/024022).
Steward et al., *Adv Colloid Interfac* 86:195-267 (2000).

* cited by examiner

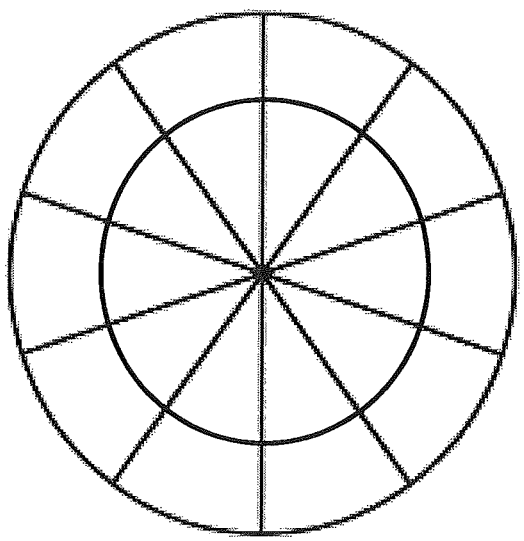

BENZOXABOROLE-CONTAINING COATING RESISTANT TO CELLULOSE-SUPPORTABLE FUNGUS

CROSS-REFERENCE TO RELATED APPLICATION

This application claims priority from application Ser. No. 62/201,836 that was filed on Aug. 6, 2015, whose disclosures are incorporated herein by reference.

TECHNICAL FIELD

The present invention contemplates a latex paint composition that contains an effective amount of one or more cellulose-supportable fungus growth-inhibiting benzoxaborole compounds of Formula C.

BACKGROUND ART

Fungi are eukaryotic microorganisms. Fungi can occur as yeasts, molds, including mildews, or as a combination of both forms. Yeasts are microscopic fungi consisting of solitary cells that reproduce by budding. Molds, in contrast, occur in long filaments known as hyphae, which grow by apical extension. Hyphae can be sparsely septate to regularly septate and possess a variable number of nuclei. Regardless of their shape or size, fungi are all heterotrophic and digest their food externally by releasing hydrolytic enzymes into their immediate surroundings (absorptive nutrition). The words "mold" and "fungus" and "yeast" and their various grammatical forms are generally used interchangeably herein except where a particular taxon is discussed.

Molds reproduce by releasing seed-like spores into their environment. Mold spores are seemingly ubiquitous. Given a suitable environment of appropriate temperature, humidity and nutrients, spores germinate and can infect one's living space leading to decay and discoloration of affected surfaces, as well as offensive odors and allergic reactions of inhabitants. [McGinnis et al., "Introduction to Mycology", In: Baron S, editor, *Medical Microbiology*, 4th ed., Galveston, Tex., University of Texas Medical Branch at Galveston (1996).]

Many fungi can grow on wood products, ceiling tiles, cardboard, wallpaper, carpets, drywall (plasterboard or wallboard), fabric, plants, foods, insulation, decaying leaves and other organic materials, causing rot or decay of the cellulosic material. Such wood product-growing fungi are referred to herein as cellulose-supportable fungi. They possess specific enzymes that can digest cellulose and related polysaccharides. These fungi can typically also utilize another source of sugars for growth, but share an ability to grow on cellulose as a food source.

There is no universal antifungal/antimicrobial that is effective at inhibiting the growth of all fungal species. Even the inhibitory efficacy of known broad spectrum antifungals depends on the species of the organism (fungi in the case of antifungal), the environmental condition (e.g., temperature and humidity), and the substrate (e.g., food source). For example, as shown herein, antifungals can display very different inhibitory efficacy for cellulose-supportable fungi when the food source (paper/cellulosic substrate vs. potato dextrose broth) or the antifungal delivery system (inside dried latex paint matrix vs. in liquid culture medium) are different.

Fungal growths, or colonies, can start to grow on a damp surface within 24 to 48 hours. Fungi digest organic material, eventually destroying the material they grow on, and then spread to destroy adjacent organic material. In addition to the damage fungi can cause in a home, they can also cause mild to severe health problems.

Of the thousands of fungi that exist, some are or produce known allergens (aggravating or causing skin, eye, and respiratory problems), and a few fungi produce harmful mycotoxins that can cause serious problems. But all fungi, in the right conditions and at high enough concentrations, are capable of adversely affecting human health.

The potential for health problems occurs when people inhale large quantities of the airborne mold spores. For some people, however, a relatively small number of mold spores can cause health problems. Fungal infection can also occur on the skin of a person's body. Infants, children, immune-compromised patients, pregnant women, individuals with existing respiratory conditions, and the elderly are at higher risks for adverse health effects from mold.

Some of the common molds (fungi) present in indoor environments that can have an impact on human health are: *Stachybotrys chartarum, Alternaria alternata, Penicillium chrysogenum, Aspergillus niger, Chaetomium globosum* and *Auerobasidium pullulans*.

The more serious health problems have been associated with the cellulose-supportable toxic black mold, *Stachybotrys atra* also called *Stachybotrys chartarum*. The mold is greenish-black and slimy, resembling tar or black paint. Spores of *Stachybotrys chartarum* are allergenic just like the spores from other mold species. *Stachybotrys chartarum* is classified as a toxic mold because it produces toxic chemicals called mycotoxins.

*Stachybotrys* typically feeds and grows only on repeatedly wetted materials that contain cellulose—from paper to ceiling tiles, drywall and any kind of wood. In most cases, this mold can be removed by a thorough cleaning with a 10% bleach solution. Severe mold infestations may require the assistance of a professional with experience in dealing with *Stachybotrys*. *Dealing With Mold & Mildew In Your Flood Damaged Home*, U.S. Department of Homeland Security, FEMA, fema.gov/pdf/rebuild/recover/fema_mold_brochure_english.pdf.

*Alternaria alternata* is another commonly encountered cellulose-supportable allergenic fungus. Brown segmented mycelia give rise to simple or solitary conidiophores, which may produce solitary apical spores, or a string of spores. *Alternaria* is one of the main allergens affecting children. In temperate climates, airborne *Alternaria* spores are detectable from May to November, with peaks in late summer and autumn.

Although *A. alternata* can be found on foodstuffs and textiles, with favorite habitats being soils, corn silage, rotten wood, compost, bird nests, and various forest plants. It is frequently found on water condensed on window frames. It is one of the most common mold spores found in dwelling dust in both North America and Europe.

The number of allergens in *A. alternata* extracts can range from 10 to 30, and few allergens are present in nearly all extracts studied [De Vouge et al., *Int Arch Allergy Immunol* 116(4):261-268 (1998)]. The presence of specific allergens, including the major allergens, depends very much on the growth conditions, and may vary during the growth cycle, being higher one day than another [Breitenbach et al., *Chem Immunol* 81:48-72 (2002); Portnoy et al., *J Allergy Clin Immunol* 91:773-782 (1993)]. Furthermore, the major allergens are secreted proteins, whereas the other allergens are intracellular proteins, and these are presented to the immune system in the spores of this mold, which are too large to reach the alveoli of the lung [Breitenbach et al., *Chem Immunol* 81:48-72 (2002)].

*Penicillium* is a common fungal contaminant in indoor environments. The spores of this mold are produced in dry chains and can easily be dispersed in the air. One of the most common species is *Penicillium chrysogenum* that produces several toxins of moderate toxicity, are allergenic and can infect immunocompromised individuals. *Penicillium chrysogenum* has been shown to induce a more robust allergic and inflammatory response at lower doses than house dust mite [Ward et al., *Indoor Air* 20:380-391 (2010)]. Thus, *Penicillium chrysogenum* and other common household molds, may play an important role in asthma development.

*Aspergillus* is another ubiquitous fungal contaminant whose spores can often be isolated from indoor air, but does not normally cause illness on healthy individuals. Allergens produced by *Aspergillus niger* and *Aspergillus fumigatus* can produce allergic reactions in humans. Aspergillosis is a group of diseases that can result from *aspergillus* infection. Individuals who suffer from asthma and other respiratory diseases are at a greater risk for these infections.

*Aureobasidium* is another common mold found in soil, wood, textiles, and indoor air environments. This yeast-like fungus is commonly found on caulking or damp window frames. Chronic exposure to *Aureobasidium pullulans* can lead to hypersensitivity pneumonitis. [*Microorganisms in Home and Indoor Work Environments: Diversity, Health Impacts, Investigation and Control*, Second Ed., Flannigan et al. Eds., Taylor and Francis Group, New York, 2011].

Other common indoor/environmental fungal contaminants include various species of *Penicillium, Nucor, Uloclardium, Trichoderma, Acremonium, Chaetomium, Aspergillus, Cladosporium, Epicoccum, Rhizopus,* and *Aureobasidium* [Horner et al., *Appl. Environ. Microbiol.* 70:6394-6400 (2004); Andersen et al., *Appl. Environ. Microbiol.* 77:4180-4188 (2011)], which are commonly isolated from indoor air and water damaged building materials. Many of the above fungi are known to produce cellulases and cause the degradation of paper and other cellulosic materials [Jerusik, *Fungal Biol. Rev.* 24:68-72 (2010)].

Latex paint is a general term that covers paints that use synthetic polymers such as acrylic, vinyl acrylic (PVA), styrene-acrylic, and the like as film-forming binders that are dispersed along with a colorant in an aqueous medium as the vehicle. The word "latex" is used because these paints form milky white emulsions in water when free of other pigments, just as does the true latex formed from a *Hevea* rubber plant.

A clear coating like a varnish primarily contains the binder and the vehicle. If a colorant such as a pigment is added to provide color and opacity to a varnish, one makes a paint.

Many commercially available latex paints contain fungus growth-inhibiting ingredients. Aside from usually-observed differences in activity against microbes such as fungi that are exhibited in aqueous media, incorporation of a fungus growth-inhibiting ingredient (fungicide) can provide a greater challenge to fungus growth inhibition relative to that exhibited in a Petri dish because of the encapsulation of the fungicide within the matrix of a dried paint film.

In the conventional model of an external paint film, there is a reservoir of fungicidal/antifungal active agent in the paint film, and there is also some biocide on the surface of the paint. As rain falls on the surface of the paint film, it washes away the biocide on the surface; however the biocide at the surface of the film is replenished by new biocide that is drawn from the reservoir. [Brown, "The Development of High-Performance Paint Film Biocides for Architectural Coatings", *Paint & Coatings Industry*, BNP Media (Jul. 1, 2014).]

When there is a balance between the biocide rate of depletion from the surface and the biocide rate of migration from within the film, the coating will have long-term protection from microbial attack. When there is not a balance, the coating will fail more quickly.

Where the selected biocide has too high a water solubility, the coating will be well protected during an initial period of perhaps 12 to 18 months, but the biocide reservoir in the film will be quickly depleted and the coating will fail after that short initial period. Where the selected biocide has too low a water-solubility and a coated surface is first placed in the outdoor environment, there is an initial period where the coating will have high susceptibility to fungal attack because some of the non-fungicidal small-molecule paint ingredients leach from the coating film and serve as a nutrient source for the fungi. After the nutrients are washed away and the coating becomes less susceptible to fungal attack, if the fungicide selected has too low a water solubility, fungi can start to become established during the initial period of high susceptibility. In this case, there is biocide present at the surface of the film, but not enough biocide migrates from the biocide reservoir in the film to prevent the fungi from becoming established.

One common strategy for achieving long-term protection of the coating film is to combine a very low water solubility fungicide with a relatively high water solubility fungicide. The more water-soluble fungicide will migrate quickly through the film and will prevent the fungi from becoming established during the initial period of the coating's high microbial susceptibility. Over longer term of outdoor exposure, the less water-soluble biocide will continue to slowly migrate from the biocide reservoir in the coating film to the coating surface. Because the coating has lower microbial susceptibility after the initial time period, the level of the less-soluble biocide delivered to the coating's surface is sufficient to prevent microbial defacement. With this strategy, long-term protection of the coating can be achieved. [Brown, "The Development of High-Performance Paint Film Biocides for Architectural Coatings", *Paint & Coatings Industry*, BNP Media (Jul. 1, 2014).]

The Brown article lists ten typical fungicides and algaecides used in the paint industry for dry film preservation. The article grouped the antifungal compounds by relative solubility in water to include: zinc pyrithione (ZnPT) [or zinc omadine (ZnOM)], chlorothalonil (CTL), carbendazim (BCM), and Irgarol® as low water solubility compounds (6-8 mg/L); diuron, dichlorooctylisothiazolinone (DCOIT), and terbutryn as having medium solubility in water [14-35 mg/L]; and octylisothiazolinone (OIT), n-butyl-benzisothiazolinone (BBIT), and iodopropynylbutyl-carbamate (IPBC) as having high water solubility [168-700 mg/L].

Illustrative solubilities of six commercially available fungicidal agents used in surface coating applications, including some of those noted by Brown, are listed in Table 1 hereinafter. Brown characterized IPBC and OIT as being among those fungicides exhibiting "high water solubility" that would be formulated with another less water soluble fungicide. Following Brown's guideline, one would classify chlorothalonil and thiabendazole as having "low water solubility" whereas triclosan would have extremely "high water solubility".

Benzoxaborole preparations and uses are the subject of several U.S. Patents, including U.S. Pat. Nos. 7,582,621; 7,767,657; 7,816,344; and 8,168,614. Many of those compounds are used as antibiotics, with U.S. Pat. No. 7,816,344 teaching at column 1, lines 37-41, certain classes of oxaboroles of Formula A, below, that are monosubstituted at the -3, 6- or -7 position or disubstituted at the 3-/6-, or -3/-7 positions

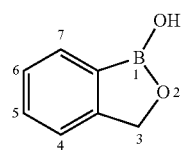

A are effective anti-bacterial agents.

U.S. Pat. No. 7,767,657 teaches and claims that a 5-fluorobenzoxyborole of Formula B and

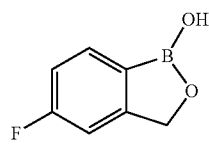

B its salts are useful in a composition for topical or foliar administration to an animal suffering from an infection from a microorganism, and particularly exemplifies yeasts and fungi as the microorganism treated. 5-Fluorobenzoxyborole is an antifungal agent in that it suppresses the ability of fungal growth, inter alia, by inhibiting leucyl-transfer RNA synthetase, an enzyme that plays a pivotal role in fungal protein synthesis.

An ethanolic solution containing 5% (w/w) 5-fluorobenzoxy-borole is commercially available for treating onychomycosis of the toenail due to *Trichophyton rubrum* or *Trichophyton mentagrophytes* from Anacor Pharmaceuticals, Inc., under the name Kerydin®. The United States Adopted Names (USAN) name for 5-fluorobenzoxyborole is tavaborole.

U.S. Patent Publication No. 20140259230 published Sep. 11, 2014 teaches the use of several oxaborole compounds for protecting plants and plant propagation materials from phytopathogens. One group of oxaboroles were disclosed to be those of Formula B-1 in which the possible combinations of R,

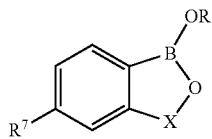

B-1

$R^7$ and X amount to more than 100 million compounds.

Those substituents in a further preferred embodiment were F for $R^7$, $CH_2$ for X and H was R, $C_1$-$C_4$alkyl optionally substituted by —$NR^3R^4$ wherein $R^3$ and $R^4$ are each independently hydrogen, optionally substituted $C_1$-$C_4$alkyl. A composition containing a compound of Formula B-1 was said to be useful in a method of protecting plants or plant propagation materials against phytopathogenic fungi belonging to several classes. The above published application teaches the use of several oxaboroles at concentrations ranging from 200 to 20 parts per million (ppm) to obtain between 80 and 20 percent control of fungal growth on infected plants, seeds and plant propagation materials.

As disclosed hereinafter, it has been found that a benzoxaborole of Formula C can be successfully added to a latex paint composition to provide protection from fungal growth on a non-living cellulosic substrate.

BRIEF SUMMARY OF THE INVENTION

The present invention contemplates a fungus-resistant latex paint composition. A contemplated fungus-resistant latex paint composition contains the typical amounts of aqueous vehicle, film-forming binder, pigment and other additives as is commonly found in commercial latex paint, but also further contains a cellulose-supportable fungus growth-inhibiting amount of a benzoxaborole of Formula C, below,

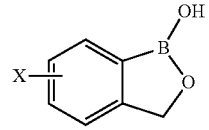

C where X is H (hydrido), halogen (fluoro, chloro or bromo), $C_1$-$C_6$ hydrocarbyl, $C_1$-$C_7$ acyl, cyano, carboxyl [C(O)OH], $C_1$-$C_6$ hydrocarbyloxy carboxylate [C(O)O$C_1$—$C_6$ hydrocarbyl], carboxamido whose amido nitrogen atom is unsubstituted [C(O)NH2], mono-substituted with a $C_1$-$C_6$ hydrocarbyl group ($R^1$) [C(O)NH$R^1$], di-substituted with a second, same or different $C_1$-$C_6$ hydrocarbyl group ($R^2$) [C(O)N$R^1R^2$], or the amido group nitrogen atom together with $R^1$ and $R^2$ form a 5- or 6-membered ring that can contain one additional hetroatom that is oxygen or nitrogen and wherein the nitrogen atom when present in that ring can be unsubstituted or substituted with one $C_1$-$C_6$ hydrocarbyl group. A typical amount of a benzoxaborole of Formula C is about 5 to about 2,000 μg/mL or about 0.005 to about 2.0 g/L.

A method of inhibiting the growth of cellulose-supportable fungus on a cellulosic surface free of visible fungal growth is also contemplated. That method comprises the step of coating a cellulose-based surface that is free of visible fungus growth, preferably an interior wall or ceiling surface, with a latex paint as described above that contains a cellulose-supportable fungus growth-inhibiting amount of a benzoxaborole of Formula C.

Another aspect of the invention is a method of inhibiting the growth of a cellulose-supportable fungus on a cellulosic surface that has a visible fungus infection. In this method, the fungus-infected surface, preferably an interior wall or ceiling surface, is painted over with a latex paint as described above that contains a fungus growth-inhibiting amount of a benzoxaborole of Formula C, particularly where "n" is 1. It has been found that this contemplated paint composition is particularly useful for painting over a fungus-infected interior wall or ceiling surface as compared to using the same paint with the currently available antifungal additives such as chlorothalonil, captan, triclosan, IPBC, OIT, and thiabendazole.

The present invention has several benefits and advantages.

One benefit is that the use of a contemplated benzoxaborole additive provides fungus protection when utilized in a latex paint.

An advantage of the invention is that the relatively high water solubility of a contemplated benzoxaborole permits easy formulation of an antifungal agent into a latex paint, particularly a latex paint intended for use in coating interior walls or ceilings.

A particular benefit of the invention is that in many cases, a latex paint containing a contemplated benzoxaborole additive performed better than did a similar paint formulated with an equal amount of another commercial antifungal additive, such as chlorothalonil, captan, octylisothiazolinone (OIT), 3-iodo-2-propynylbutyl-carbamate (IPBC), thiabenzaole, and triclosan, in that it not only provided superior fungal growth inhibition to an initial fungal infection, but also suppressed fungal growth "bleed through" when painted over a fungus-infected surface.

A particular advantage of the invention is that a benzoxaborole antifungal is usually colorless, and it generally does not interfere with the integrity of the paint mixture (e.g., spiking the benzoxaborole compounds tested herein does not appear to change the viscosity, color, or performance of the paint).

Another benefit of the invention is that a contemplated benzoxaborole additive appears to be UV-stable so that the antifungal protection in paint will not decrease rapidly due to prolonged UV-exposure.

Another advantage of the invention is that it is not necessary to use two antifungals with high and low water solubilities for long term benefits.

Still further benefits and advantages of the invention will be apparent to those skilled in the art from the description that follows.

BRIEF DESCRIPTION OF THE DRAWING

In the drawing forming a portion of this description,

FIG. 1 is a depiction of a circular filter paper disc divided into 20 sections of equal area that is used to estimate the percentage of defacement of a painted surface area caused by fungal growth.

DETAILED DESCRIPTION OF THE INVENTION

A fungus-resistant latex paint composition is contemplated by the present invention. Such a contemplated fungus-resistant latex paint composition contains the typical amounts of vehicle (water), film-forming binder, pigment and other additives that are found in a commercially available latex paint, but also further contains a cellulose-supportable mold (fungal) growth-inhibiting (effective) amount of one or more benzoxaboroles of Formula C, below,

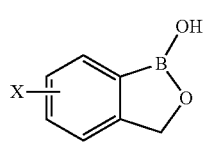

C where X is H (hydrido), $C_1$-$C_7$ acyl, cyano, halogen (fluoro, chloro or bromo), $C_1$-$C_6$ hydrocarbyl, carboxyl [C(O)OH], $C_1$-$C_6$ hydrocarbyloxy carboxylate [C(O)O$C_1$-$C_6$ hydrocarbyl], carboxamido whose amido nitrogen atom is unsubstituted [C(O)NH2], mono-substituted with a $C_1$-$C_6$ hydrocarbyl group ($R^1$) [C(O)NH$R^1$], di-substituted with a second, same or different $C_1$-$C_6$ hydrocarbyl group ($R^2$) [C(O)N$R^1R^2$], or the amido group nitrogen atom together with $R^1$ and $R^2$ form a 5- or 6-membered ring that can contain one additional heteroatom that is oxygen or nitrogen and wherein the nitrogen atom when present in that ring can be unsubstituted or substituted with one $C_1$-$C_6$ hydrocarbyl group. A substituent X preferably has a positive Hammett sigma constant for one or both of para and meta substituents. A halogen or a $C_1$-$C_6$ hydrocarbyl group is a preferred substituent, and that substituent is preferably bonded at position 5 of a compound of Formula C, below.

A contemplated latex paint composition is preferably free of a cellulose-supportable fungus growth-inhibiting amount of a second antifungal agent (i.e., a non-Formula C antifungal agent). A typical amount of a benzoxaborole of Formula C is about 5 to about 2,000 µg/mL or about 0.005 to about 2.0 g/L. More preferably, that amount is about 10 to about 500 µg/mL.

The substituent "X" is preferably in the 5-position of a compound of Formula C. The ring numbering for a compound of Formula C is shown in the structural formula below

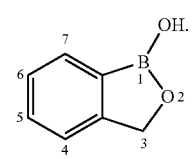

C

The structural formula of a preferred compound of Formula C is shown by the compounds of structural Formula C-1, below, where X is as defined above.

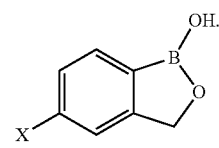

C-1

Structural formulas of illustrative compounds of Formula C-1 are shown below along with alpha-numeric designations.

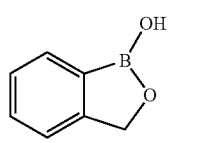

B0

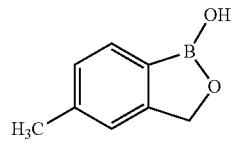

B1

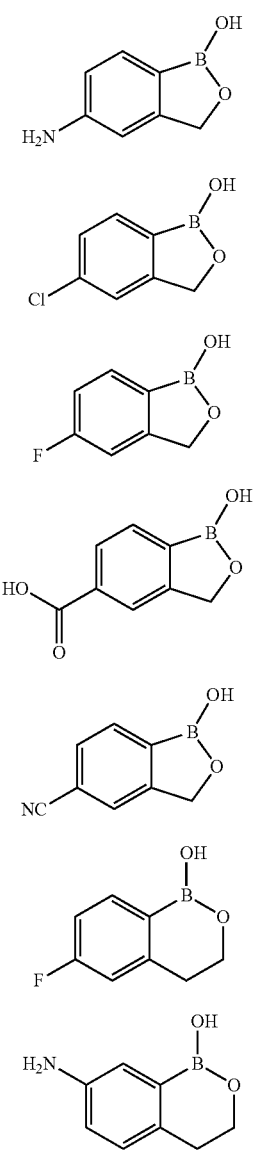

A paint contains three main categories of ingredients: film-forming binder, vehicle and pigment. In a latex paint, the vehicle is typically water in which the binder and pigment are dispersed. Additional ingredients can also be present as discussed below.

The binder imparts properties such as gloss, durability, flexibility, and toughness. Binders include natural resins and oils such as shellac and linseed oil, as well as synthetic polymers and co-polymers such as alkyds, acrylics, vinyl-acrylics, styrenated acrylics (styrene/acrylic and/or methacrylic co-polymer), vinyl acetate/ethylene (VAE), polyurethanes, polyesters, melamine resins, epoxy, or oils. One hundred percent acrylic, styrenated acrylic and vinyl-acrylic binders are preferred in latex paints. A latex paint binder typically constitutes about 25 to about 45% volume solids (VS) of the paint [VS=100×(Volume of pigment+Volume of solid binder)/Total wet paint volume].

Illustrative, useful, latex paint polymers, their component monomers, their individual coalescing temperatures and glass transition properties are disclosed in U.S. Pat. Nos. 4,069,186, 4,277,385, 4,283,320, and 4,800,107, and are discussed in Steward et al., *Adv Colloid Interfac* 86:195-267 (2000).

Pigment volume concentration (PVC) is a measure of the pigment quantity in a paint [PVC=100×Volume of pigment/(Volume of pigment+Volume of solid binder)]. Flat paints have a very high pigment loading and have high PVCs (often of about 35% to about 80%, and more usually about 35% to about 50%). Primers and undercoats vary from 30% to about 50% PVC as do semi-gloss, satin and low sheen paints. Gloss colored paints can vary from 3% to about 20% PVC depending on the color of the paint.

Binders can be categorized according to the mechanisms for drying or curing. Although drying may refer to evaporation of the solvent or thinner, it usually refers to oxidative cross-linking of the binder resins and is indistinguishable from curing.

A latex paint is a water-borne dispersion of sub-micrometer polymer particles. These dispersions are prepared in water by emulsion polymerization.

Latex paints cure by a process called coalescence where first the water, and then the trace, or coalescing, solvent, evaporate and draw together and soften the binder particles and fuse them together into irreversibly bound, film-forming networked structures, so that the paint does not re-dissolve in the solvent/water that originally carried it. The residual emulsifying surfactants in paint, as well as hydrolytic effects with some polymers cause the paint to remain susceptible to softening and, over time, degradation by water.

The main purpose of the diluent (vehicle) is as the carrier for the non-volatile components. Thus, the vehicle disperses the polymer and pigment, and adjusts the viscosity of the paint. The vehicle is volatile and does not become part of the paint film. The vehicle also controls flow and application properties, and in some cases can affect the stability of the paint while in liquid state.

Pigments are finely ground granular solids incorporated in the paint to contribute color. Fillers are granular solids incorporated to impart toughness, texture, give the paint special properties, or to reduce the cost of the paint. Alternatively, some paints contain dyes instead of or in combination with pigments.

Pigments can be classified as either natural or synthetic. Natural pigments include various clays, calcium carbonate, mica, silicas, and talcs. Synthetic pigments include engineered molecules, calcined clays, blanc fixe, precipitated calcium carbonate, and synthetic pyrogenic silicas.

Hiding pigments, in making paint opaque, also protect the substrate from the harmful effects of ultraviolet light. Hiding pigments include titanium dioxide, phthalo blue, red iron oxide, and many others.

Fillers are a special type of pigment that serve to thicken the film, support its structure and increase the volume of the paint. Fillers are usually inexpensive and inert materials, such as diatomaceous earth, talc, lime, barytes, clay, and similar compounds.

Besides the three main categories of ingredients (binder, vehicle and pigment), paint can have a wide variety of miscellaneous additives that are usually added in small amounts, and yet can provide a significant effect on the product. Some examples include additives to modify surface tension, improve flow properties, improve the finished appearance, increase wet edge, improve pigment stability as with hydroxypropyl cellulose, impart antifreeze properties using polyols such as ethylene glycol and propylene glycol, control foaming, and control skinning. Other types of additives include catalysts, thickeners, stabilizers, emulsifiers, texturizers, adhesion promoters, UV stabilizers, flatteners (de-glossing agents), and biocides to fight microbial growth. Additives normally do not significantly alter the percentages of individual components in a formulation. Illustrative latex paint compositions can be found in U.S. Pat. Nos. 3,215,660, 3,483,148, and 7,482,395.

Also included herein as a latex paint is a latex paint primer. A primer is a paint that is applied directly to the bare substrate. Primers have varying roles on different substrates. The main functions of a primer include providing adhesion to the substrate for the new paint system and providing a surface to which subsequent coats of paints can easily adhere. A primer is often used to seal the surface and prevent subsequent coats of paint from sinking into the substrate and losing gloss.

Primers are usually pigmented and typically have a middle range pigment volume concentration (PVC) of about 35-45%. This pigment level permits a primer to have spare binder resin (left over from pigment holding together duties) for adhesion to substrate purposes. A relatively large pigment content is needed to provide hiding power and to help seal off the substrate surface.

A method of inhibiting the growth of a cellulose-supportable fungus on a cellulosic surface is also contemplated. That method comprises the step of coating a surface that is free of visible fungus growth with a latex paint as described above that contains a cellulose-supportable fungus growth-inhibiting amount of a benzoxaborole of Formula C. The coated surface is preferably an interior (indoor) wall or ceiling that contains cellulose.

The surface to be coated is itself cellulosic such as the paper-coated exterior surfaces of drywall (plasterboard). That surface can have one or more previously applied and dried coats of paint, or be paint-free as in a newly erected plasterboard wall or ceiling, a cellulosic ceiling tile, cardboard, wallpaper, or similar building material.

Another aspect of the invention is a method of inhibiting the growth of cellulose-supportable fungus on a painted surface that has a visible fungus infection. In this method, the cellulose-supportable fungus-infected cellulosic surface, preferably an interior (indoor) wall or ceiling surface as discussed above, is painted over with a latex paint as described above that contains a cellulose-supportable fungus growth-inhibiting amount of a benzoxaborole of Formula C. It has been found that a contemplated paint composition is particularly useful for painting over a fungus-infected cellulosic wall or ceiling surface as compared to using the same paint with a currently available antifungal agent such as chlorothalonil, thiabendazole, OIT, triclosan, and IPBC.

In a composition discussed above, it is preferred that the antifungal compound of Formula C that is used be a compound of Formula C-1. More preferably still, X of Formula C-1 is a halogen such as fluorine or chlorine or $C_1$-$C_6$ hydrocarbyl.

The word "hydrocarbyl" is used herein as a short hand term for a non-aromatic group that includes straight and branched chain aliphatic as well as cyclic groups or radicals that contain only carbon and hydrogen. Inasmuch as alicyclic groups are cyclic aliphatic groups, such substituents are deemed to be subsumed within the aliphatic groups. Thus, alkyl, alkenyl and alkynyl groups are contemplated.

Usual chemical suffix nomenclature is followed when using the word "hydrocarbyl" except that the usual practice of removing the terminal "yl" and adding an appropriate suffix is not always followed because of the possible similarity of a resulting name to that of one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, and cyclohexenyloxy groups.

A contemplated cyclohydrocarbyl substituent ring contains 3 to 6 carbon atoms. A preferred cyclohydrocarbyl substituent is a cycloalkyl group. The term "cycloalkyl" means a cyclic alkyl radical that is saturated. Examples of such cycloalkyl radicals include cyclopropyl, cyclobutyl, cyclopentyl, 2-methylcyclopentyl, cyclohexyl and the like.

Where a specific aliphatic hydrocarbyl substituent group is intended, that group is recited; i.e., $C_1$-$C_4$ alkyl, methyl or tert-butyl. Exemplary hydrocarbyl groups contain a chain of 1 to 6 carbon atoms, and preferably 1 or 4 carbon atoms. A $C_1$, methyl, group is most preferred.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein. Where a specific aliphatic hydrocarbyl substituent group is intended, that group is recited; i.e., $C_1$-$C_4$ alkyl, methyl or 2-propyl.

Examples of straight and branched chain alkyl radicals include methyl, ethyl, n-propyl, isopropyl, n-butyl, isobutyl, sec-butyl, tert-butyl, pentyl and hexyl. Illustrative cyclic alkyl groups include cyclopropyl, cyclopentyl, 3-methylcyclopentyl and cyclohexyl. Examples of suitable alkenyl radicals include ethenyl (vinyl), 2-propenyl, 3-propenyl, 1,4-butadienyl, 1-butenyl, 2-butenyl, and 3-butenyl, 2-pentenyl and 3-hexenyl. Examples of alkynyl radicals include ethynyl, 2-propynyl, 1-propynyl, 1-butynyl, 2-butynyl, 3-butynyl, and 1-methyl-2-propynyl, 3-methyl-1-butynyl and 2-methyl-1-pentynyl. Cyclic alkynes are analogous to the cyclic alkenes.

As a skilled worker will understand, a substituent that cannot exist such as a $C_1$ alkenyl or alkynyl group or a $C_1$-$C_2$ cyclic group is not intended to be encompassed by the word "hydrocarbyl", although such substituents with two or more carbon atoms are intended for other than cyclic substituents.

A hydrocarbyl group containing a —C(O)-functionality such as a keto group or a portion of a carboxyl group is referred to as a hydrocarboyl (acyl) group. Exemplary hydrocarboyl (acyl) groups include acyl groups such as formyl, acetyl, propionyl, butyryl, and valeryl, 4-methylvaleryl. A $C_1$-$C_6$ hydrocarbyl ester of a carboxyl group is referred to herein, for example, as a $C_1$-$C_6$ hydrocarbyloxy carboxylate.

A typical amount of a benzoxaborole of Formula C used in an antifungal (mold growth-inhibiting or fungus growth-inhibiting) paint is about 5 to about 2,000 μg/mL, and more preferably about 10 to about 500 μg/mL. It is presently preferred that a compound of Formula C be the only anti-cellulose-supportable mold growth-inhibiting additive present in a contemplated paint composition.

Of the contemplated benzoxaborole compounds, the water solubility of only Compound B9 has been determined. That value is 800 mg/L. It is believed that the other compounds of Formula C-1 have similar solubilities in water.

The specific fungus species whose infection of a painted surface is inhibited can depend on the geographical location of that surface. Thus, more generally, those fungi whose growth is to be inhibited on a surface that is painted with a latex paint containing a contemplated benzoxaborole illustratively include one or more of the following genera: *Alternaria, Aspergillus, Aureobasidium, Rhizopus, Mucor, Penicillium, Cladosporium, Epicoccum, Chaetomium, Acre-* monium, Ulocladium, Fusarium and Stachybotrys. Specific fungi whose growth is to be inhibited include one or more of Alternaria alternata, Aspergillus niger, Aspergillus fumigatus, Aureobasidium pullulans, Rhizopus spp., Mucor spp., Penicillium brevicompactum, Penicillium corylophilum, Penicillium purpurogenum, Penicillium chrysogenum, Cladosporium spp., Epicoccum spp., Chaetomium globosum, Acremonium spp., Ulocladium spp., Fusarium oxysporum and Stachybotrys chartarum.

Results

Several studies of the growth inhibition of cellulose-supportable fungi have been undertaken that illustrate the antifungal application of a contemplated benzoxaborole compound of Formula C when present in a dried latex paint formulation. The results of those studies are presented below.

Initial data for a 3-day minimal inhibitory concentration (MIC) determinations against various common indoor/environmental fungi cultured in aqueous media using microtiter plates are shown in Table 1, below, along with water-solubility data for some commercial fungicidal compounds as well as various antifungal agents based on Formula C-1.

TABLE 1

| Antifungal Compound | 3 day MIC μg/mL 25% PDB* | | Solubility in water (mg/L) |
|---|---|---|---|
| | Alternaria alternata | Stachybotrys chartarum | |
| Captan | 1.6 | 0.39 | 3.3 |
| Chlorothalonil | 0.78 | <0.1 | <100 |
| IPBC[a] | 0.8 | 0.8 | 156 |
| OIT[b] | 200 | 0.1 | 500 |
| Thiabendazole | 100 | 25 | 8 |
| Triclosan | 6.3 | <0.1 | 12,000 |
| B0 | 12.5 | 0.5 | — |
| B9 | 1.6 | 0.13 | 800 |
| B8 | 3.1 | 0.13 | — |
| B1 | 6.3 | 0.5 | — |
| B5 | 200 | 6.3 | — |
| B6 | 200 | 64 | — |
| B7 | >200 | 25 | — |
| B10 | 200 | 100 | — |
| B11 | 100 | 12.5 | — |
| | Aspergillus niger | Aspergillus fumigatus | |
| Captan | 16 | 12.5 | 3.3 |
| Chlorothalonil | 0.4 | 0.2 | <100 |
| IPBC[a] | — | 0.4 | 156 |
| Thiabendazole | 12.5 | 6.25 | 8 |
| B0 | 2.0 | 0.5 | — |
| B9 | 0.25 | 0.5 | 800 |
| B8 | 0.25 | 0.5 | — |
| B1 | 2.0 | 0.25 | — |
| B6 | >64 | >64 | — |
| | Penicillium brevicompactum | Penicillium corylophilum | |
| Captan | 0.78 | 0.78 | 3.3 |
| Chlorothalonil | <0.1 | 0.39 | <100 |
| IPBC[a] | 0.4 | 0.20 | 156 |
| OIT[b] | <0.1 | <0.1 | 500 |
| Thiabendazole | 0.4 | 0.39 | 8 |
| Triclosan | 3.1 | 3.13 | 12,000 |
| B0 | 1.6 | 3.13 | — |
| B9 | 0.2 | 0.39 | 800 |
| B8 | 0.4 | 0.78 | — |
| B10 | >200 | >200 | — |
| B11 | 50 | 100 | — |

TABLE 1-continued

| Antifungal Compound | 3 day MIC μg/mL 25% PDB* | | Solubility in water (mg/L) |
|---|---|---|---|
| | Penicillium purpurogenum | Penicillium chrysogenum | |
| Captan | 0.78 | 0.78 | 3.3 |
| Chlorothalonil | 0.78 | <0.1 | <100 |
| IPBC[a] | <0.1 | 0.2 | 156 |
| OIT[b] | <0.1 | <0.1 | 500 |
| Thiabendazole | 0.20 | 0.4 | 8 |
| Triclosan | 3.13 | 6.3 | 12,000 |
| B0 | 6.3 | 3.13 | — |
| B9 | 0.78 | 0.50.4 | 800 |
| B8 | 1.56 | 0.50.8 | — |
| B10 | >200 | >200 | — |
| B11 | 25 | 100 | — |
| | Mucor spp. | Rhizopus spp. | |
| Captan | 3.1 | 12.5 | 3.3 |
| Chlorothalonil | 0.8 | 0.8 | <100 |
| Thiabendazole | >200 | 400 | 8 |
| B0 | 0.5 | 4.0 | — |
| B9 | 0.25 | 0.5 | 800 |
| B8 | 0.5 | 4.0 | — |
| B1 | 1.0 | 16.0 | — |
| B6 | >64 | >64 | — |
| | Aureobasidium pullulans | Fusarium oxysparum ST-33 | |
| Captan | 0.8 | 2 | 3.3 |
| Thiabendazole | 0.4 | 25 | 8 |
| B0 | 1.0 | 1.0 | — |
| B9 | 0.125 | 0.25 | 800 |
| B8 | 0.125 | 0.25 | — |
| B1 | 1.0 | 1.0 | — |
| B6 | >64 | >64 | — |
| | Cladosporium cladosporioides | Aspergillus flavus | |
| Captan | — | 25 | 3.3 |
| Chlorothalonil | — | 0.2 | <100 |
| Thiabendazole | 0.8 | 12.5 | 8 |
| B0 | 0.5 | 2 | — |
| B9 | 0.1 | 1 | 800 |
| B8 | 0.1 | 1 | — |
| B1 | — | 2 | — |
| B6 | — | >64 | — |

*PDB = Potato dextrose broth.
[a]IPBC = 3-Iodo-2-propynylbutylcarbamate;
[b]OIT = 2-Octyl-4-isothiazolin-3-one In reviewing the data in Table 1, it is noted with interest that Compounds B5 and B7 are structurally similar to the compounds consisted of 5-membered ring compounds (5 atoms in the ring structure that includes the boron atom) such as Compounds B9 and B8, but Compounds B5 and B7 exhibited much lower antifungal activity in aqueous solution; i.e., at least an order of magnitude difference in MIC values. Compound B5 can be viewed as a homolog of Compound B9, having an extra $CH_2$ group in one ring, whereas Compound B7 can be viewed as a combination of a homolog (as in B5) with a "ring-walked" identical substituent as compared to Compound B6.

Using the MIC and water-solubility as guides, several latex paint formulations were prepared using a benzoxaborole of Formula C as well as commercially available antifungal compounds as potential antifungal additives in latex paints. The results of several studies are shown in Tables 2 and 3 for three representative architectural/indoor fungi. Table 2 lists results for paint formulations coated twice on both sides of a cellulosic surface of a filter paper disc to provide a surface that is visibly free of any fungal growth after the paint coating has dried. Table 3 lists results for a painted cellulosic surface in which fungal growth was painted over by a contemplated latex paint containing an antifungal additive as disclosed herein.

A Defacement Rating is measured by estimating the percentage of surface defacement with 10 being no defacement and 0 begin completely defaced. [American Society for Testing and Materials (ASTM) test method D3273-12 [Standard Method for Resistance to Growth of Mold on the Surface of Interior Coatings in an Environmental Chamber; ASTM D3273-12, American Society for Testing Materials International, West Conshohocken, Pa., USA].

TABLE 2

| Treatment Description* | Average defacement rating ± standard deviation (number of samples) Exposure Time; days | | |
|---|---|---|---|
| | 7 | 14 | 21 |
| *Stachybotrys chartarum*** | | | |
| +0 "as is"[1] | 1.5 ± 1.5 (24) | 0.0 ± 0.0 (24) | 0.0 ± 0.0 (24) |
| +0 "as is"[2] | 8.4 ± 3.1 (9) | 7.1 ± 5.7 (9) | 6.5 ± 3.2 (9) |
| +0 "as is"[3] | 10.0 ± 0.4 (9) | 10.0 ± 0.4 (9) | 9.9 ± 0.6 (9) |
| +0 "as is"[4] | 0.0 ± 0.0 (9) | 0.0 ± 0.0 (9) | 0.0 ± 0.0 (9) |
| +0 "as is"[5] | 9.4 ± 1.1 (9) | 0.5 ± 0.7 (9) | 0.5 ± 0.7 (9) |
| +10 µg/mL B8 | 5.7 ± 4.9 (3) | 0.0 ± 0.0 (3) | 0.0 ± 0.0 (3) |
| +100 µg/mL B8 | 9.9 ± 0.4 (9) | 8.1 ± 1.9 (9) | 7.1 ± 2.6 (9) |
| +100 µg/mL B9 | 9.9 ± 0.3 (12) | 4.4 ± 2.9 (12) | 2.0 ± 2.8 (12) |
| +100 µg/mL B0 | 0.7 ± 1.3 (12) | 0.0 ± 0.0 (12) | 0.0 ± 0.0 (12) |
| +100 µg/mL Captan | 2.9 ± 3.3 (12) | 0.0 ± 0.0 (12) | 0.0 ± 0.0 (12) |
| +100 µg/mL Chlorothalonil | 5.8 ± 3.0 (9) | 0.8 ± 1.8 (9) | 0.6 ± 1.7 (9) |
| +100 µg/mL IPBC | 9.9 ± 0.3 (15) | 8.1 ± 1.5 (15) | 6.1 ± 2.7 (15) |
| +100 µg/mL OIT | 9.9 ± 0.3 (18) | 8.2 ± 2.5 (18) | 6.9 ± 2.4 (18) |
| +100 µg/mL Thiabendazole | 1.3 ± 0.3 (12) | 0.0 ± 0.0 (12) | 0.0 ± 0.0 (12) |
| +100 µg/mL Triclosan | 0.8 ± 1.4 (12) | 0.0 ± 0.0 (12) | 0.0 ± 0.0 (12) |
| *Alternaria alternata*** | | | |
| +0 "as is"[1] | 0.9 ± 1.8 (18) | 0.7 ± 1.7 (18) | 0.4 ± 1.7 (18) |
| +0 "as is"[2] | 9.5 ± 0.0 (9) | 9.0 ± 0.6 (9) | 8.6 ± 0.6 (9) |
| +0 "as is"[3] | 10.0 ± 0.0 (9) | 9.9 ± 0.4 (9) | 9.5 ± 0.6 (9) |
| +0 "as is"[4] | 0.0 ± 0.0 (3) | 0.0 ± 0.0 (3) | 0.0 ± 0.0 (3) |
| +0 "as is"[5] | 0.0 ± 0.0 (3) | 0.0 ± 0.0 (3) | 0.0 ± 0.0 (3) |
| +10 µg/mL B8 | 5.0 ± 1.0 (9) | 4.7 ± 1.2 (9) | 4.7 ± 1.2 (9) |
| +100 µg/mL B8 | 9.9 ± 0.4 (12) | 8.1 ± 1.5 (12) | 7.8 ± 1.5 (12) |
| +100 µg/mL B9 | 7.4 ± 1.8 (9) | 3.8 ± 0.9 (9) | 3.8 ± 0.9 (9) |
| +100 µg/mL B0 | 2.3 ± 2.3 (15) | 0.5 ± 1.8 (15) | 0.0 ± 0.0 (15) |
| +100 µg/mL Captan | 0.1 ± 0.3 (12) | 0.0 ± 0.0 (12) | 0.0 ± 0.0 (12) |
| +100 µg/mL IPBC | 9.9 ± 0.4 (9) | 8.4 ± 2.7 (9) | 7.5 ± 3.4 (9) |
| +100 µg/mL Chlorothalonil | 1.9 ± 2.4 (15) | 0.5 ± 1.8 (15) | 0.5 ± 1.8 (15) |
| +100 µg/mL OIT | 8.1 ± 0.3 (15) | 6.9 ± 1.0 (15) | 4.9 ± 0.7 (15) |
| +100 µg/mL Thiabendazole | 0.0 ± 0.0 (15) | 0.0 ± 0.0 (15) | 0.0 ± 0.0 (15) |
| +100 µg/mL Triclosan | 0.1 ± 0.4 (15) | 0.0 ± 0.0 (15) | 0.0 ± 0.0 (15) |
| *Penicillium chrysogenum*** | | | |
| +0 "as is"[1] | 5.1 ± 2.1 (18) | 0.1 ± 0.3 (18) | 0.0 ± 0.0 (18) |
| +0 "as is"[4] | 9.2 ± 1.4 (9) | 0.2 ± 0.4 (9) | 0.0 ± 0.0 (9) |
| +100 µg/mL B0[1] | 2.7 ± 0.8 (6) | 0.0 ± 0.0 (6) | 0.0 ± 0.0 (6) |
| +200 µg/mL B0[1] | 10.0 ± 0.0 (3) | 6.8 ± 4.0 (3) | 5.0 ± 5.5 (3) |
| +200 µg/mL B0[4] | 10.0 ± 0.0 (6) | 6.8 ± 4.0 (6) | 5.0 ± 5.5 (6) |
| +100 µg/mL B9[1] | 3.7 ± 1.5 (6) | 0.0 ± 0.0 (6) | 0.0 ± 0.0 (6) |
| +200 µg/mL B9[1] | 10.0 ± 0.0 (6) | 9.8 ± 0.4 (6) | 6.7 ± 3.9 (6) |
| +200 µg/mL B9[4] | 10.0 ± 0.0 (3) | 10.0 ± 0.0 (3) | 9.7 ± 0.6 (3) |
| +100 µg/mL B8[1] | 7.3 ± 1.3 (9) | 0.0 ± 0.0 (9) | 0.0 ± 0.0 (9) |
| +200 µg/mL B8[1] | 10.0 ± 0.0 (6) | 9.5 ± 1.2 (6) | 8.7 ± 2.3 (6) |
| +100 µg/mL Captan[1] | 3.2 ± 1.8 (6) | 0.0 ± 0.0 (6) | 0.0 ± 0.0 (6) |
| +200 µg/mL Captan[1] | 9.8 ± 0.4 (6) | 2.3 ± 3.9 (6) | 1.7 ± 4.1 (6) |
| +200 µg/mL Captan[1] | 5.3 ± 4.0 (3) | 0.0 ± 0.0 (3) | 0.0 ± 0.0 (3) |
| +100 µg/mL Chlorothalonil[1] | 4.9 ± 1.9 (6) | 0.0 ± 0.0 (6) | 0.0 ± 0.0 (6) |
| +200 µg/mL Chlorothalonil[1] | 8.3 ± 1.4 (6) | 0.8 ± 2.0 (6) | 0.0 ± 0.0 (6) |
| +200 µg/mL Chlorothalonil[4] | 10.0 ± 0.0 (3) | 5.3 ± 0.6 (3) | 0.3 ± 0.6 (3) |
| +100 µg/mL IPBC[1] | 10.0 ± 0.0 (6) | 9.4 ± 0.4 (6) | 9.4 ± 0.4 (6) |
| +200 µg/mL IPBC[1] | 10.0 ± 0.0 (6) | 10.0 ± 0.0 (6) | 9.3 ± 0.8 (6) |
| +200 µg/mL IPBC[4] | 10.0 ± 0.0 (3) | 10.0 ± 0.0 (3) | 10.0 ± 0.0 (3) |
| +100 µg/mL OIT[1] | 10.0 ± 0.0 (9) | 10.0 ± 0.0 (9) | 9.3 ± 1.5 (9) |
| +200 µg/mL OIT[1] | 10.0 ± 0.0 (6) | 10.0 ± 0.0 (6) | 9.8 ± 0.4 (6) |
| +200 µg/mL OIT[4] | 10.0 ± 0.0 (3) | 10.0 ± 0.0 (3) | 10.0 ± 0.0 (3) |
| +100 µg/mL Thiabendazole[1] | 4.1 ± 0.0 (9) | 0.4 ± 0.4 (9) | 0.0 ± 0.0 (9) |
| +200 µg/mL Thiabendazole[1] | 9.3 ± 1.2 (6) | 4.0 ± 4.7 (6) | 1.7 ± 3.6 (6) |
| +200 µg/mL Thiabendazole[4] | 10.0 ± 0.0 (3) | 9.3 ± 1.2 (3) | 4.7 ± 4.6 (3) |
| +100 µg/mL Triclosan[1] | 1.8 ± 1.4 (9) | 0.0 ± 0.0 (9) | 0.0 ± 0.0 (9) |
| +200 µg/mL Triclosan[1] | 9.3 ± 0.5 (6) | 0.2 ± 0.4 (6) | 0.0 ± 0.0 (6) |

TABLE 2-continued

| Treatment Description* | Average defacement rating ± standard deviation (number of samples) Exposure Time; days | | |
|---|---|---|---|
| | 7 | 14 | 21 |
| +200 µg/mL Triclosan[4] | 4.0 ± 3.6 (3) | 0.0 ± 0.0 (3) | 0.0 ± 0.0 (3) |

*[1]Olympic ® Home; [2]Valspar ® Ceiling (no additive); [3]Valspar ® Bonding Primer; [4]Valspar ® QuikHide (with mildewcide); [5]Sherwin-Williams Property Advantage ® (no additive).
**for *Stachybotrys chartarum* and *Alternaria alternata*, the chemicals (tested for antifungal activity) were mixed only into Olympic ® Home paint. For *Penicillium chrysogenum*, the chemicals were mixed into either Olympic ® Home paint or Valspar ® QuikHide paint.

The capability to inhibit fungus growth with an antifungal additive in water-based latex paints was evaluated using either Olympic® Home interior flat latex paint (PPG Industries, Pittsburgh, Pa.) or Valspar® QuikHide white flat interior paint (The Valspar Corporation, Minneapolis, Minn.). According to the product label and information sheet, Olympic® Home paint does not contain an antimicrobial additive. In contrast, both Valspar® ceiling paint and Valspar® QuikHide paint both contain mildewcidal additives according to a representative from the company's Customer Support department. Sherwin-Williams Property Advantage® interior paint "does not contain anti-microbials and is not a mildew proof product" according to a representative from the company's Customer Support department.

The data (Tables 2 and 4) show that by themselves ('as is'; using paint straight out of the can without any modification), significant fungal/mold growth was observed in less than seven days on the surface of the painted cellulose-based substrate that had two coats of Olympic® Home paint, or Valspar® QuikHide. It is noted that Valspar® QuikHide paint, which contains some level of added mildewcide, was not effective at inhibiting fungal growth under these experimental conditions (elevated humidity and temperature). It is also noted that this study subjected a treated surface to a very high level of freshly prepared fungal inoculum, meaning that the experimental condition used presented a very challenging system (strongly encourages fungal/mold growth) for anti-mildew/antifungal samples.

Table 2 shows that two coats of Property Advantage® or Valspar® Ceiling paint were not able to prevent fungal/mold growth after 14 days under the experimental conditions (Valspar® Ceiling paint did show inhibition for *Alternaria alternata*, but not as much for *Stachybotrys chartarum*). Valspar® bonding primer was able to resist fungal/mold growth for over 21 days.

Valspar® bonding primer behaved as if it contained an antimicrobial agent. However, that could not be confirmed by company representatives. It is also likely that this product contains a higher percentage of organic solvents in its composition, creating a less favorable environment to support living organisms.

Based on the 'as is' data in Table 2, Olympic® Home and Valspar® QuikHide paints were selected as representative basic paint formulations into which additional antifungal compounds were admixed, because neither of these two paints exhibited any fungal/mold growth inhibition under the experimental conditions. Three common indoor/architectural fungal/mold species (*Alternaria* alternata, *Stachybotrys chartarum*, and *Penicillium chrysogenum*) were used to represent fungal/mold contaminants that one might find in a typical architectural structure.

For painted surfaces (using Olympic® Home paint by itself) contaminated with *Alternaria alternata* spores, the average defacement ratings (mold coverage level) was 0.9±1.8 over 18 samples in just 7 days after fungal spore inoculation (Table 2). The defacement levels were very high for the unaltered paint at the 14 and 21 day time points. The average defacement rating was essentially 0 (100% fungus coverage), suggesting no capability to inhibit fungal growth.

Against *Stachybotrys chartarum*, which has a slower growth rate than *Alternaria alternata*, the surfaces painted with unaltered paint ("as is") were almost all covered in fungus growth just 7 days after the samples were inoculated with the spores of *Stachybotrys chartarum*. The average defacement rating of these samples is 1.5±1.5 over 24 samples (Table 2).

Valspar® QuikHide paint, which contains a proprietary antimicrobial additive, also performed poorly for inhibiting the growth of *Stachybotrys chartarum* and *Alternaria alternata* on painted surfaces (i.e., complete fungal coverage/defacement after just 7 days). Both Olympic® Home and Valspar® QuikHide paints failed to inhibit the growth of *Penicillium chrysogenum* past 7 days after fungal inoculation. Sherwin-Williams Property Advantage® interior paint also failed to inhibit fungal growth 7-14 days after being inoculated with the spores of *Stachybotrys chartarum* or *Alternaria alternata*.

As shown in Table 2, the filter paper discs separately painted with the same Olympic® Home interior flat latex paint that was pre-mixed with Compounds B9 or B8 performed significantly better at resisting fungal/mold growth on the painted surfaces; i.e., the difference was greater than 2 standard deviations.

Against *Alternaria alternata*:

Seven days after fungal inoculation, 12 dried discs coated with two coats of paint that contained 100 µg/mL of Compound B8 yielded an average defacement rating of 9.9±0.4 (Table 2). This means that the paint impregnated with Compound B8 completely inhibited fungal/mold growth after 7 days, whereas the unaltered 'as is' samples (without B8) showed complete fungal defacement. After 21 days, the average defacement rating for the 12 discs was 7.8±1.5 (approximately 78% of the disc surface was free of fungal growth). Table 2 also show that 10 µg/mL of Compound B8 provided much less ability to inhibit fungal growth. Thus, a preferred antifungal surface coating composition would contain more than 10 µg/mL of the antifungal benzoxaborole additive.

After one week, the averaged defacement rating on samples containing 100 µg/mL of Compound B9 was found to be 7.4±1.8 for 9 samples. After 21 days, an average defacement value of 3.8±0.9 was found. In other words, about 38% of the painted surfaces containing 100 µg/mL of Compound B9 were free of fungal growth. Compound B0 did not show any significant ability to inhibit fungal growth on the painted surface at the 100 µg/mL concentration level despite showing complete inhibition of fungal growth at 12.5 µg/mL in a liquid medium (Table 1).

As will be discussed in greater detail in later sections, comparisons between results of Table 1 and Table 2 show that the efficacy of an antifungal compound in the matrix of a dried surface coating formulation is very different from the efficacy of the same compound in a liquid composition. This is true for both benzoxaboroles and non-benzoxaborole antifungal agents. Therefore, there is no clear correlation permitting one to accurately predict the inhibitory activity of an antifungal agent in a dried paint matrix using data obtained in a liquid medium.

The effectiveness of incorporating benzoxaborole antifungal agents into a paint matrix to prevent fungal growth on a painted surface was also examined by comparisons with other commercially available antifungal agents that have been used for preventing microbial growth in surface coatings. Painted surfaces coated with paints containing 100 μg/mL of IPBC were able to resist mold growth to the same degree as either of Compounds B8 or B9 over the 21 days trial period (Table 2).

However, paints containing captan completely failed to inhibit fungal growth within 7 days (averaged defacement rating=0.1±0.3 over 12 samples). Thus, paints containing 100 μg/mL of captan completely failed to inhibit fungal growth on the dried painted surfaces even though the MIC value for captan in a liquid medium was 1.6 μg/mL (Table 1). The same results were found for painted discs that had 100 μg/mL of chlorothalonil (liquid MIC value=0.78 μg/mL), triclosan (liquid MIC value=6.3 μg/mL), and thiabendazole liquid MIC value=100 μg/mL). Chlorothalonil, tricolosan, and thiabendazole all showed no inhibitory activity towards fungal/mold growth on the painted surfaces when present dispersed within that painted surface.

Interestingly, paint containing 100 μg/mL of OIT (liquid MIC value=200 μg/mL) demonstrated good control for preventing fungal growth when present within a painted surface. After 7 days, the averaged defacement rating for 15 painted discs was found to be 8.1±0.3 (about 81% free of fungal growth). Even after 21 days, the averaged defacement rating for 15 painted discs was found to be 4.9±0.7 (about 50% clear of fungal growth). Again, these results show a lack of a clear correlation between antifungal activity observed in liquid and in dried surface coating.

Against *Stachybotrys chartarum*:

Latex paints containing 100 μg/mL of Compound B8 or Compound B9 were effective at preventing fungal growth on painted cellulose-based surfaces. Seven days after fungal inoculation, averaged defacement ratings of 9.9±0.3 and 9.9±0.4 were found for samples with Compounds B9 and B8, respectively (Table 2). Surfaces with two coats of paint containing 100 μg/mL of Compound B8 continued to provide good prevention of fungal growth for 21 days. After 21 days, the averaged defacement rating for 9 painted discs was found to be 7.7±2.6 (about 77% of surface free of fungal growth). In contrast, Compound B9 showed good fungal growth inhibition on painted surfaces for 14 days, but failed to maintain any antifungal activity after 21 days. Paints containing 10 μg/mL of Compound B8 were not very effective at preventing fungal growth on painted surfaces. Thus, a preferred antifungal surface coating composition should contain more than 10 μg/mL of the antifungal benzoxaborole additive.

Despite demonstrating good antifungal activity in liquid medium, Compound B0 (liquid medium MIC=0.5 μg/mL against *Stachybotrys chartarum*; Table 1) did not inhibit the growth of *Stachybotrys chartarum* as an antifungal additive present in dried paint.

Against *Stachybotrys chartarum*, paints containing 100 μg/mL of IPBC performed similarly to paint containing 100 μg/mL of Compound B8 or Compound B9. Discs with two coats of paints containing 100 μg/mL of IPBC showed very little fungal growth after 7 days (averaged defacement rating of 9.9±0.3 over 15 samples), and continued to maintain good prevention of fungal growth for 21 days (averaged defacement rating of 6.1±2.7 over 15 samples). OIT-containing paints also displayed a similar level of fungal growth inhibition. OIT and IPBC can be considered industry standards because they have been used as anti-mildew/antimicrobial additives for various surface coating products. The data in Table 2 show that antifungal benzoxaboroles, such as B8 and B9, demonstrated similar antifungal activity as OIT and IPBC in a surface coating matrix (i.e. latex paint).

Other antifungal compounds that have been used as antifungal/antimildew additives for surface protecting products were also assayed under the same experimental conditions using 100 μg/mL of each. Captan, chlorothalonil, thiabendazole, and triclosan were all unable to inhibit fungal growth on painted discs after 7 days. Again, captan (liquid medium MIC=0.39 μg/mL; Table 1), chlorothalonil (liquid medium MIC<0.1 μg/mL; Table 1), thiabendazole (liquid medium MIC=25 μg/mL; Table 1), and triclosan (liquid medium MIC<0.1 μg/mL; Table 1) all demonstrated very high antifungal activity in liquid culture conditions (Table 1). Some of these compounds showed better antifungal activity against *Stachybotrys chartarum* in liquid cultures than did Compounds B8 and B9. These results further demonstrated that antifungal or antimicrobial chemicals can behave very unpredictably inside a dried surface coating matrix. An antifungal chemical might completely lose its antifungal activity when it is inside a dried surface coating matrix.

Against *Penicillium chrysogenum:*

For *Penicillium chrysogenum*, two different paints were used as the base into which antifungal agents were mixed. Table 2 shows that discs containing two coats of Olympic® Home or Valspar® QuikHide paint performed similarly. Neither of the two paints was able to inhibit fungal growth past 7 days. Furthermore, data obtained from mixing the chemicals into Valspar® QuikHide paint were comparable to those obtained using Olympic® Home paint.

For the antifungal benzoxaborole compounds (B0, B8, and B9), 200 μg/mL was needed to obtain a good level of fungal growth prevention under the experimental conditions (Table 2). At the 200 μg/mL level, paints containing B0 provided a significant amount of antifungal efficacy up to 14 days after fungal inoculation. Paints containing 200 μg/mL of Compound B8 exhibited complete inhibition of fungal growth on the painted discs after 7 days (averaged defacement rating of 10.0±0.0 over 9 samples), and the painted surfaces continued to show good levels of antifungal efficacy after 21 days. Paints containing 200 μg/mL of Compound B9 showed good levels of fungal growth inhibition.

Paints containing 200 μg/mL of Captan or OIT were unable to provide decent inhibition of fungal growth on the surfaces of painted discs past 7 days. Paints containing 200 μg/mL of thiabendazole were unable to prevent fungal growth on the surfaces of painted discs past 14 days. Paints containing 200 μg/mL of chlorothalonil did not perform much better at preventing fungal growth on the surfaces. However, paints containing 100 or 200 μg/mL of IPBC were very effective at preventing the growth of *Penicillium chrysogenum* on the painted surfaces, even after 21 days. Similar to the tests with *Alternaria alternata* and *Stachybotys chartarum*, the observed antifungal efficacy for *Penicillium chrysogenum* on dried painted surfaces (Table 2) showed no obvious correlation to the antifungal efficacy observed in a liquid medium (Table 1).

TABLE 3

| Treatment Description | Average defacement rating ± standard deviation (number of samples) Exposure Time; days | | |
|---|---|---|---|
| | 7 | 14 | 21 |
| *Stachybotrys chartarum** | | | |
| +0 "as is" | 2.4 ± 2.9 (9) | 2.2 ± 3.1 (9) | 2.2 ± 3.1 (9) |
| +100 µg/mL B8 | 7.0 ± 1.9 (9) | 6.4 ± 2.6 (9) | 5.4 ± 2.3 (9) |
| +10 µg/mL B9 | 0.3 ± 0.6 (3) | 0.0 ± 0.0 (3) | 0.0 ± 0.0 (3) |
| +100 µg/mL B9 | 7.2 ± 2.6 (9) | 1.3 ± 3.0 (9) | 1.0 ± 2.8 (9) |
| +100 µg/mL B0 | 6.1 ± 3.3 (9) | 4.4 ± 3.0 (9) | 3.9 ± 2.9 (9) |
| +100 µg/mL Captan | 0.0 ± 0.0 (6) | 0.0 ± 0.0 (6) | 0.0 ± 0.0 (6) |
| +100 µg/mL IPBC | 1.2 ± 1.3 (9) | 0.0 ± 0.0 (9) | 0.0 ± 0.0 (9) |
| +100 µg/mL Thiabendazole | 0.7 ± 1.6 (6) | 0.2 ± 0.8 (6) | 0.2 ± 0.8 (6) |
| +100 µg/mL Chlorothalonil | 2.2 ± 2.1 (9) | 2.0 ± 1.7 (9) | 2.0 ± 1.7 (9) |
| +100 µg/mL Triclosan | 0.7 ± 1.2 (9) | 0.7 ± 1.2 (9) | 0.6 ± 1.0 (9) |
| +100 µg/mL OIT | 4.6 ± 3.2 (9) | 3.6 ± 3.7 (9) | 3.0 ± 3.7 (9) |
| *Alternaria alternata** | | | |
| +0 "as is" | 1.8 ± 1.9 (9) | 1.3 ± 1.3 (9) | 1.2 ± 1.2 (9) |
| +100 µg/mL B8 | 7.1 ± 2.2 (9) | 3.4 ± 2.9 (9) | 3.0 ± 2.8 (9) |
| +200 µg/mL B8 | 9.3 ± 1.2 (3) | 7.3 ± 2.9 (3) | 3.0 ± 0.9 (3) |
| +100 µg/mL B9 | 7.2 ± 1.1 (12) | 5.1 ± 2.1 (12) | 4.6 ± 2.2 (12) |
| +200 µg/mL B9 | 9.7 ± 0.6 (3) | 7.0 ± 4.4 (3) | 6.3 ± 5.5 (3) |
| +100 µg/mL B0 | 2.1 ± 1.6 (6) | 1.0 ± 1.3 (6) | 0.4 ± 0.6 (6) |
| +100 µg/mL Captan | 3.6 ± 3.9 (9) | 2.5 ± 4.0 (9) | 2.4 ± 3.8 (9) |
| +100 µg/mL IPBC | 5.9 ± 2.9 (9) | 3.1 ± 2.4 (9) | 3.0 ± 2.5 (9) |
| +100 µg/mL Thiabendazole | 0.0 ± 0.0 (6) | 0.0 ± 0.0 (6) | 0.0 ± 0.0 (6) |
| +1000 µg/mL Thiabendazole | 7.3 ± 1.3 (10) | 3.6 ± 1.7 (10) | 2.8 ± 1.1 (10) |
| +1000 µg/mL Chlorothalonil | 0.5 ± 1.4 (9) | 0.2 ± 0.5 (9) | 0.1 ± 0.3 (9) |
| +100 µg/mL Triclosan | 3.6 ± 3.5 (9) | 2.6 ± 3.7 (9) | 2.0 ± 2.9 (9) |
| +100 µg/mL OIT | 0.3 ± 0.5 (6) | 0.0 ± 0.0 (6) | 0.0 ± 0.0 (6) |
| *Penicillium chrysogenum** | | | |
| +0 "as is" | 0.8 ± 1.3 (9) | 0.0 ± 0.0 (9) | 0.0 ± 0.0 (9) |
| +200 µg/mL B8 | 2.3 ± 0.6 (9) | 0.0 ± 0.0 (9) | 0.0 ± 0.0 (9) |
| +200 µg/mL B9 | 8.7 ± 1.0 (9) | 2.6 ± 3.1 (9) | 0.0 ± 0.0 (9) |
| +200 µg/mL B0 | 0.0 ± 0.0 (9) | 0.0 ± 0.0 (9) | 0.0 ± 0.0 (9) |
| +200 µg/mL Captan | 0.0 ± 0.0 (9) | 0.0 ± 0.0 (9) | 0.0 ± 0.0 (9) |
| +200 µg/mL IPBC | 6.9 ± 3.8 (9) | 4.8 ± 4.0 (9) | 3.1 ± 3.4 (9) |
| +200 µg/mL Thiabendazole | 6.7 ± 4.6 (9) | 2.2 ± 4.4 (9) | 2.2 ± 4.4 (9) |
| +200 µg/mL Chlorothalonil | 0.0 ± 0.0 (9) | 0.0 ± 0.0 (9) | 0.0 ± 0.0 (9) |
| +200 µg/mL Triclosan | 0.9 ± 2.7 (9) | 0.0 ± 0.0 (9) | 0.0 ± 0.0 (9) |
| +200 µg/mL OIT | 3.6 ± 2.8 (9) | 3.0 ± 3.7 (9) | 2.3 ± 40.0 (9) |

*for *Stachybotrys chartarum* and *Alternaria alternata*, the chemicals (tested for antifungal activity) were mixed into Olympic ® Home paint for the study. For *Penicillium chrysogenum*, the chemicals were mixed into Valspar ® QuikHide paint for the study.

The benzoxaborole antifungal agents also worked very well to inhibit existing fungal growth on painted or treated surfaces. In this series of experiments, fungal growth was allowed to cover a painted surface (surface containing 2 coats of the unaltered paint) to a defacement rating of 3-5, forming a 'contaminated surface'. These contaminated surfaces were then painted over with one coat of the same paint either with or without antifungal additives to completely cover the appearance of the existing fungus growth (resulting in a defacement rating of 10 [no visual fungal growth] on the re-painted surfaces). The paint application was extended approximately 1-2 cm beyond the edge of the disc onto the NSA medium. Each formulation used a separate brush to avoid cross contamination. The re-painted discs were placed back into the humid environment with elevated temperature to encourage fungal growth.

Table 3 shows that one week after re-painting and maintenance under high humidity and elevated temperature incubating conditions, latex paints containing either Compound B8 (100 µg/mL; averaged defacement rating=7.1±2.2 in 9 samples) or Compound B9 (100 µg/mL; averaged defacement rating=7.2±1.1) demonstrated a good ability to inhibit the re-emergence of *Alternaria alternata* fungal/mold growth on the re-painted surfaces. Discs re-painted with paints containing Compound B9 continued to demonstrate a good level of antifungal control over 21 days.

Contaminated surfaces that were re-painted with paints containing 200 µg/mL of Compounds B8 or B9 showed even greater ability to inhibit the re-emergence of fungal/mold growth. Comparatively, the fungus-containing samples that were painted over with the un-modified paint ('as is') yielded an average defacement rating of 1.8±1.9 after one week of incubation. In other words, the fungi/molds were able to completely reclaim the samples where 2 coats of un-modified paints were re-painted over the contaminated surfaces. However, when the contaminated surfaces were re-painted with a paint composition containing antifungal benzoxaborole, the re-emergence of fungus/mold growth was inhibited significantly.

This suppression of fungus/mold re-emergence observed when an extra coating of paint was applied onto a contaminated surface (Table 3) is very different from the antifungal effect shown in Table 2, which evaluates the antifungal efficacy of paint dried on a surface visually absent of fungus/mold growth. Table 3 shows complete re-emergence of fungus/mold (*Alternaria alternata*) growth in 7 days when contaminated surfaces were re-painted with paints containing 100 µg/mL of Compound B0, IPBC, triclosan, thiabendazole, OIT, or captan.

Re-painting a contaminated surface with 1000 µg/mL (10 times higher concentration than all other treatments) chlorothalonil was also insufficient to completely prevent the re-emergence of fungus/mold growth in 7 days. In contrast, chlorothalonil can completely inhibit the growth of *Alternaria alternata* at 1000 times lower concentration in liquid medium (MIC=0.78 µg/mL; Table 1). Also, it should be noted that Table 2 shows paints containing 100 µg/mL of OIT or IPBC to have good antifungal activity when the paints were applied to clean cellulose-based discs prior to the introduction of fungal spore inoculum.

When painting over surfaces contaminated by *Stachybotrys chartarum*, paints containing 100 µg/mL of the antifungal benzoxaborole compounds (B0, B8, and B9) were effective at significantly reducing the re-emergence of fungus/mold on re-painted surfaces (Table 3). In fact, contaminated surfaces that were painted over with paints containing 100 µg/mL of Compound B8 managed to suppress fungus/mold re-emergence by about 50% for 21 days (averaged defacement rating of 5.4±2.3 in 9 samples). Comparatively, contaminated surfaces painted over with two coats of unaltered paints were completely covered in fungus/mold within 7 days. Contaminated surfaces painted over with 2 coats of paint containing 100 µg/mL of captan, IPBC, thiabendazole, chlorothalonil, OIT, or triclosan were also unable to inhibit the re-emergence of fungus/mold growth past 7 days. Furthermore, contrary to what one might predict based on the liquid medium MIC values in Table 1, painting over contaminated surfaces with paints containing 100 µg/mL of Compound B1, B5, B6, or B7 showed very little ability to inhibit *Stachybotrys chartarum* re-emergence on the surfaces after 7 days.

A similar trend was observed when re-painting surfaces contaminated by *Penicillium chrysogenum*. In this case, paints containing 200 μg/mL of Compound B8 provided mild inhibitory activity for the re-emergence of fungus/mold on re-painted discs after 7 days. Paints containing 200 μg/mL of Compound B9 provided good inhibitory activity for the re-emergence of fungus/mold on re-painted discs after 7 days. Even, against a faster growing fungus, such as *Penicillium chrysogenum*, benzoxaborole antifungals can provide some degree of control for treating a contaminated surface.

In comparison, contaminated surfaces re-painted with two coats of unaltered paints showed complete surface coverage of fungus/mold growth after 7 days (averaged defacement rating of 0 in 9 samples). Painting over contaminated surfaces with paints containing 200 μg/mL of captan, IPBC, thiabendazole, chlorothalonil, OIT, or triclosan were unable to provide statically significant suppression of fungus/mold re-emergence within 7 days. This was unexpected because Table 2 shows very good antifungal activity for paints containing IPBC, OIT and thiabendazole. None of the treatments were able to significantly suppress the re-emergence of *Penicillium chrysogenum* after 14 days.

Overall, the benzoxaborole-containing latex paint's ability to inhibit the re-emergence of fungus growth on a re-painted contaminated surface (with no decontamination steps taken prior to painting over) compares favorably against other antifungal agents. The data from Tables 1, 2 and 3 do not show a clear correlation between water solubility, MIC value determined in liquid medium, and antifungal activity in a dried latex paint formulation for the group of antifungal compounds examined. In other words, the antifungal efficacy determined in liquid media or other means (such as disk diffusion) does not necessarily correlate with the antifungal efficacy of the antifungal agents when incorporated into a water-based latex paint matrix, especially when considering the antifungal efficacy of a dried painted surface. The lack of an obvious correlation between Tables 2 and 3 further suggests the unique character of a surface coating composition's ability to suppress fungus/mold re-emergence by directly painting over a contaminated cellulose-based surface.

This study found the antifungal benzoxaborole compounds to be a singular class of compounds because they demonstrated good antifungal efficacy in three areas: in liquid medium (Table 1), in dried latex paint formulation for preventing fungus/mold growth (Table 2), and in dried latex paint formulation for suppressing the re-emergence of fungus/mold growth when painting over a contaminated surface (Table 3). All the other industry standard antifungal additives tested can only satisfy 1 or 2 of the above three areas, and none of them seems to be capable of suppressing the re-emergence of fungus/mold growth on a contaminated surface.

In a separate study, painted filter paper discs were irradiated with UV light from a 30 watt bulb for 2 hours and then inoculated with *Alternaria alternata* spores ("+UV" in the table below), or were inoculated without prior UV irradiation ("no UV" in the Table 4). The painted filter papers were incubated as discussed elsewhere herein, evaluated at 13 and 21 days post-inoculation for defacement by fungal growth and compared to similar painted filter paper discs that were not irradiated prior to inoculation. The results of this study are shown below in Table 4.

Briefly, once incorporated into the water-based latex paint mixture, coated onto a surface and dried, the benzoxaborole antifungal was stable against UV light exposure. The antifungal capacity of painted surfaces exposed to UV irradiation was the same as surfaces not exposed to UV irradiation. Under the experimental condition, this was also observed with painted samples containing IPBC, which is the active ingredient found in BIOBAN™ IPBC antimicrobial products including paint, stain, cordage coating, plastic, plastic coating, paper coating, and wood preservative to inhibit fungus/mildew growth.

TABLE 4

| Treatment Description | Average Defacement ± standard deviation for 3 replicates Exposure Time (days) | |
|---|---|---|
| | 13 | 21 |
| *Alternaria alternata* | | |
| +0 "as is" - no UV | 0.0 ± 0.0 | 0.0 ± 0.0 |
| +100 μg/mL B9 - no UV | 10.0 ± 0.0 | 9.0 ± 0.0 |
| +100 μg/mL IPBC - no UV | 8.3 ± 2.1 | 4.0 ± 4.0 |
| +0 "as is" - +UV | 0.0 ± 0.0 | 0.0 ± 0.0 |
| +100 μg/mL B9 - +UV | 10.0 ± 0.0 | 8.3 ± 2.1 |
| +100 μg/mL IPBC - +UV | 9.7 ± 0.6 | 6.0 ± 4.4 |

*Olympic ® Home latex paint was used in this study.

Materials and Methods

Fungal Isolates and Cultures

Fungal isolates of *Alternaria alternata, Aspergillus niger, Aureobasidium pullulans, Rhizopus* spp., *Mucor* spp., *Aspergillus fumigatus, Aspergillus flavus, Penicillium* brevicompactum, *Penicillium* corylophilum, *Penicillium* purpurogenum, *Penicillium chrysogenum*, and *Fusarium oxysporum* species complex haplotype ST33 were cultured from either cryogenic storage stock, silica gel storage stock, or lyophilized (with skim milk) stock in the Plant Pathology and Environmental Microbiology Department at The Pennsylvania State University, University Park, Pa., 16802. A fungal isolate of *Stachybotrys chartarum* (ATCC 16026) was purchased from American Type Culture Collection (ATCC) Manassas, Va. A fungal isolate of *Cladosporium cladosporioides* (CBS 112388) was purchased from the CBS Fungal Biodiversity Centre, Utrecht, Netherlands. Olympic® Home interior flat latex paint (PPG Industries, Pittsburgh, Pa.), Zinsser® Perma-White mold-proof interior paint (satin; RPM International Inc., Medina, Ohio), Valspar® QuikHide White flat interior paint (The Valspar Corporation, North Kansas City, Mo.), Valspar® Ultra ceiling white flat interior paint (The Valspar Corporation, Minneapolis, Minn.), Olympic® Premium Kitchen & Bath Enamel semi-gloss white mildew resistant paint (PPG Industries, Pittsburgh, Pa.), Valspar® Tintable white glossy Bonding Primer (interior/exterior latex; The Valspar Corporation), and Property Advantage® extra white flat interior paint (The Sherwin-Williams Company, Cleveland, Ohio) were used in this study.

Antifungal and Stock Solutions

Captan, 3-Iodo-2-propynylbutylcarbamate (IPBC), chlorothalonil, and triclosan were obtained from Sigma-Aldrich (St. Louis, Mo.). Thiabendazole and 2-(hydroxymethyl)-benzene boronic acid hemiester (B0) were obtained from Alfa Aeser (Ward Hill, Mass.). 2-Octyl-4-isothiazolin-3-one (OIT) was obtained from Tokyo Chemical Industry (TCI), Tokyo, Japan. 5-Fluoro-1,3-dihydro-2,1-benzoxaborol-1-ol (B9), 5-chloro-1,3-dihydro-2,1-benzoxaborol-1-ol (B8), 1-hydroxy-1,3-dihydro-2,1-benzoxaborole-5-carbonitirile (B11), 5-Methyl-1,3-dihydro-2,1-benzoxaborol-1-ol (B1), and 1-hydroxy-1,3-dihydro-2,1-benzoxaborole-5-carboxylic acid (B10) were obtained from Enamine Ltd (Kiev, Ukraine). 6-fluoro-3,4-dihydro-1H-2,1-benzoxaborinin-1-ol (B5), 5-Amino-1,3-dihydro-2,1-benzoxaborol-1-ol (B6), and 7-amino-3,4-dihydro-1H-2,1-benzoxaborinin-1-ol (B7) were generously provided by Anacor Pharmaceuticals Inc. (Palo Alto, Calif.). All reagents were used without further modification/purification.

Stock solutions (concentrations of between 4,000 μg/mL to 10,000 μg/mL; stored at −18° C.) of the above antifungals were prepared in dimethyl sulfoxide (DMSO). The stock solutions were further diluted into sterile 25% potato dextrose broth (PDB) so that the diluted solutions could be used for the antifungal susceptibility studies. This way, a typical microdilution study would reach a final ratio of about 0.5-2% v/v of DMSO in 25% PDB. Control studies showed that 2% v/v DMSO in 25% PDB did not inhibit fungal growth for the species examined.

Inoculum Preparation

All fungal organisms were maintained on potato dextrose agar (PDA), and sufficient asexual spores can be isolated from the cultures after 1-2 weeks of incubation at room temperature (22-24° C.) with 12ON/12OFF (12 hours on and 12 hours off) fluorescent light+darklight photoperiod using fluorescent (Philips, F40LW) and blacklight (F40T12) bulbs.

Spore inocula were prepared in sterile distilled water with 0.1% Tween® 20 (a polysorbate surfactant), and a hemocytometer was used to determine the spore density. Typically, the spore inoculum was prepared fresh prior to each study, and the inoculum was appropriately diluted to a final concentration of $0.4-1\times10^5$ spores/mL or colony-forming unit (CFU)/mL in each study. The spore suspension can be stored in a refrigerator at 4° C. for up to one week.

Antifungal Susceptibility Testing and Interpretation

The minimal inhibitory concentrations (MICs) for individual antifungal agents were determined by following a modified broth microdilution protocol CLSI (Clinical and Laboratory Standards Institute) M38-A2 [Clinical and Laboratory Standards Institute (2008) *Reference method for broth dilution antifungal susceptibility testing of filamentous fungi—2$^{nd}$ edition: Approved Standard M38-A2, CLSI, Wayne, Pa.*] where 25% potato dextrose broth (PDB) was used as the medium. The studies were performed in flat bottom, 96-well microtiter plates (Greiner Bio-One, Frickenhausen, Germany).

Initially, the individual MIC values were determined in triplicate in a final volume of 0.2 mL/well with antifungal concentrations of 0-200 μg/mL (12 serial dilutions down from 200 μg/mL [200, 100, 50, 25, 12.5, 6.25, 3.13, 1.56, 0.78, 0.39, 0.20, and 0.098 μg/mL]; control studies with 0 μg/mL of antifungals were performed in parallel for each plate). Plates sealed with clear polyester film (VWR, Radnor, Pa.) were incubated at a temperature of about 25° C. The progress of fungal growth was monitored at 48 hours and 72 hours. The MICs were determined as the lowest antifungal concentrations that completely inhibited fungal growth (no visible growth) or the concentrations that inhibited fungal growth by greater than 95% (determined as relative absorbance using the Bio-Tek® PowerWave™ HT microplate reader at 530 or 630 nm) relative to the corresponding antifungal-free control.

Fungus Resistance Test for Painted Surfaces Containing Antifungal Additives

This test was used to evaluate the resistance of paint films containing antifungal additives to surface fungal growth. This procedure is adapted and modified from the American Society for Testing and Materials (ASTM) test method D3273-12 [Standard Method for Resistance to Growth of Mold on the Surface of Interior Coatings in an Environmental Chamber; ASTM D3273-12, American Society for Testing Materials International, West Conshohocken, Pa., USA] and ASTM test method G21-13 [Standard Practice for Determining Resistance of Synthetic Polymeric Materials to Fungi. ASTM G21-13, American Society for Testing and Materials, West Conshohocken, Pa., USA].

Olympic® Home interior flat latex paint (PPG Industries, Pittsburgh, Pa.) and Valspar® QuikHide White flat interior paint (Valspar Corporation, Minneapolis, Minn.) were used for all studies unless otherwise noted. Stock solutions of the antifungal additives of interest were prepared in reagent grade dimethyl sulfoxide (DMSO; Alfa Aesar, Ward Hill, Mass.). Additives were spiked (by adding appropriate amounts of the antifungal stock solutions) into the liquid paint at specified concentrations. Samples of the additive-spiked paint were vigorously mixed with a vortex mixer for at least one minute to ensure uniform dispersion of the additive in the paint. A control sample (containing just DMSO) was included with each test that did not contain any antifungal additives. Studies that use other brands of paint followed the same protocol as described for those using the Olympic® Home interior flat latex paint and Valspar® QuikHide paint.

Test surfaces were prepared in triplicate. In most cases, the tested conditions were repeated on a different date, again in triplicate. Spiked paint solutions were applied to autoclaved (for 15-20 minutes) #413 filter paper discs, 4.25 cm in diameter from VWR, Radnor, Pa. Two coats of paint were applied with a polyester brush to completely cover both faces of the filter paper disc, allowing at least four hours drying time between coats.

Nutrient-Salts Agar (NSA) medium was prepared according to ASTM method G21-13 in 100×15 mm sterile polystyrene petri dishes (VWR® Radnor, Pa.) with a solidified agar layer of about 3 to about 6 mm (⅛ to ¼ in.) in depth. The agar was allowed to solidify for at least 24 hours before being used. The painted test filter paper discs were placed in the center of the agar plates in a biosafety hood while wearing clean nitrile gloves.

The paint coatings were evaluated against three representative cellulose-supportable fungi: *Stachybotrys chartarum, Penicillium chrysogenum*, and *Alternaria alternata*. Fungal isolates of *S. chartarum* (ATCC 16026) was purchased from American Type Culture Collection (ATCC) Manassas, Va. Fungal isolates of *Alternaria alternata* and *Penicillium chrysogenum* were obtained from the Plant Pathology and Environmental Microbiology Department at Penn State University.

A sterile cell scraper (Falcon® #35085, Corning, N.Y.) was used to gently scrape the surface growth from the fungal culture. A spore suspension of each of these fungi was prepared by pouring a 20-mL portion of autoclaved deionized water containing 0.01% Tween® 20 onto a subculture of each fungal species. Spores were counted with the use of a hemocytometer (Hausser Scientific, Horsham, Pa.) under a compound light microscope. Spore suspensions of *Stachybotrys chartarum* and *Penicillium chrysogenum* were diluted to $1\times10^6$ spores/mL with autoclaved deionized water. Spore suspensions of *Alternaria alternata* were used "as is" in the range of 200,000 to 400,000 spores/mL.

Painted test surfaces were inoculated with a spray bottle or with a sterile cotton-tipped applicator. To inoculate the sample with a spray bottle, the spore suspension was sprayed twice on the painted test discs with an autoclaved spray bottle that delivered approximately 0.14 g of fluid per spray. To inoculate the sample with a cotton-tipped applicator, an autoclaved cotton-tipped applicator was submerged in approximately 400 µL of the spore inoculum solution (spore concentrations described above) and applied evenly over the surface of the painted test surface twice. A fresh autoclaved cotton-tipped applicator was used for the application of each painted disc. All the paint studies with *Alternaria alternata* and *Stachybotrys chartarum* were inoculated using the spray bottle method. For studies with *Penicillium chrysogenum* using Olympic® Home paint, the spray bottle inoculation method was used. For studies with *Penicillium chrysogenum* using Valspar® QuikHide paint, the cotton-tipped applicator inoculation method was used.

After inoculation, the NSA agar plates were sealed with Parafilm®. These plates were then placed in random order in a Percival® dew chamber model E 54-UD (Perryville, Iowa) in the dark at a temperature of 28 to 30° C. with at least 95%±5% relative humidity. Samples (in polystyrene petri dishes) were stored inverted to prevent the pooling of condensate on the sample surface.

Samples were evaluated at regular intervals. The intensity of the fungal growth was rated by estimating the percentage of surface defacement using the following ratings: 10: 0% defacement; 9=1-10% defacement; 8=11-20% defacement; 7=21-30% defacement; 6=31-40% defacement; 5=41-50% defacement; 4=51-60% defacement; 3=61-70% defacement; 2=71-80% defacement; 1=81-90% defacement; and 0=91-100% defacement. A grid that divides the circular area into 20 equal sections as shown in FIG. 1 was used to estimate the extent (percent defacement) of fungal growth.

For example, if defacement was found in 11/20 sections, a rating of 4 would be given to account for approximately 55% overall defacement. Photographs were taken of the test samples to document the observations.

Fungus Resistance Test after Painting Over Fungal Growth with Paint Containing Antifungal Additives This test was used to evaluate the ability of paint films containing antifungal additives to prevent the re-emergence of fungal growth after painting over existing growth. This procedure is adapted and modified from American Society for Testing and Materials (ASTM) test method D3273-12 (Standard Test Method for Resistance to Growth of Mold on the Surface of Interior Coatings in an Environmental Chamber) and ASTM test method G21-13 (Standard Practice for Determining Resistance of Synthetic Polymeric Materials to Fungi) that were noted previously.

Olympic® Home interior flat latex paint (PPG Industries, Pittsburgh, Pa.) and Valspar® QuikHide White flat interior paint (Valspar Corporation, Minneapolis, Minn.) were used for the experiments in this study unless specified. Stock solutions of the antifungal additives of interest were prepared in reagent grade dimethyl sulfoxide (DMSO; Alfa Aesar, Ward Hill, Mass.). Additives were spiked (by adding appropriate amounts of the antifungal stock solutions) into the liquid paint at specified concentrations. Samples of additive-spiked paint were vigorously mixed with a vortex mixer for at least one minute to insure uniform dispersion of the additive in the paint. A control sample (containing just DMSO) was included with each test that did not contain any antifungal additives. Studies that used other brands of paint followed the same protocol as described for those using the Olympic® Home interior flat latex paint.

Test surfaces were prepared in triplicate. In most cases, the tested conditions were repeated on a different date, again in triplicate. Spiked paint solutions were applied to autoclaved (for 15-20 minutes at 121° C.) #413 filter paper discs, 4.25 cm in diameter from VWR®, Radnor, Pa. Two coats of paint were applied with a polyester brush to completely cover both faces of the filter paper disc, allowing at least four hours drying time between coats.

Nutrient-Salts Agar (NSA) media was prepared according to ASTM method G21-13 in 100×15 mm sterile polystyrene petri dishes (VWR® Radnor, Pa.) with a solidified agar layer from 3 to 6 mm (⅛ to ¼ in.) in depth. The agar was allowed to solidify for at least 24 hours before being used. The painted test filter paper discs were placed in the center of the agar plates in a biosafety hood while wearing clean nitrile gloves.

The paint coatings were evaluated against three representative fungi: *Stachybotrys chartarum*, *Penicillium chrysogenum*, and *Alternaria alternata*. Fungal isolates of *Stachybotrys chartarum* (ATCC 16026) was purchased from American Type Culture Collection (ATCC) Manassas, Va. Fungal isolates of *Alternaria alternata* and *Penicillium chrysogenum* were obtained from the Plant Pathology and Environmental Microbiology Department at Penn State University.

A sterile cell scraper (Falcon® #35085, Corning, N.Y.) was used to gently scrape the surface growth from the fungal culture. A spore suspension of each of these fungi was prepared by pouring a 20-mL portion of autoclaved deionized water containing 0.01% Tween® 20 onto a subculture of each fungal species. Spores were counted with the use of a hemocytometer (Hausser Scientific, Horsham, Pa.) under a microscope. Spore suspensions of *Stachybotrys chartarum* and *Penicillium chrysogenum* were diluted to $1\times10^6$ spores/mL with autoclaved deionized water. Spore suspensions of *Alternaria alternata* were used "as is" in the range of 200,000 to 400,000 spores/mL.

Painted test surfaces were inoculated with a spray bottle or with a cotton-tipped applicator. To inoculate the sample with a spray bottle, the spore suspension was sprayed twice on the painted test discs with a spray bottle that delivered approximately 0.14 g of fluid per spray. To inoculate the sample with a cotton-tipped applicator, an autoclaved cotton-tipped applicator was submerged in approximately 400 µL of the inoculum solution and applied evenly over the surface of the painted test surface twice. All the paint studies with *Alternaria alternata* and *Stachybotrys chartarum* were inoculated using the spray bottle method. All the studies with *Penicillium chrysogenum* were inoculated with the cotton-tipped applicator method.

After inoculation, the NSA agar plates were sealed with Parafilm®. These plates were then placed in random order in a Percival® dew chamber model E 54-UD (Perryville, Iowa) in the dark at a temperature of 28 to 30° C. with at least 95±5% relative humidity. Samples (in polystyrene petri dishes) were stored inverted to prevent the pooling of condensate on the sample surface.

Samples showing similar levels of fungal growth (defined by having similar defacement rating or defacement ratings that are 1 or 2 units from each other; samples used had defacement ratings of about 3-5) were collected based on the number of samples needed for testing. These samples were randomly assigned to each of the testing categories. The paint formulation was painted over the fungal growth with one coat of paint using a nylon polyester brush to completely cover the appearance of the existing fungus growth. The paint application was extended approximately 1-2 cm beyond the edge of the disc onto the NSA medium. Each formulation used a separate brush to avoid cross contamination.

After the paint dried, the plates (containing the test discs) were sealed with Parafilm®. These plates were then placed in random order in a Percival® dew chamber model E 54-UD (Perryville, Iowa) in the dark at a temperature of 28 to 30° C. with at least 95%±5% relative humidity. Samples were stored inverted to prevent the pooling of condensate on the sample surface.

Samples were evaluated at regular intervals. The intensity of the fungal growth was rated by estimating the percentage of surface defacement using the following ratings: 10: 0% defacement; 9=1-10% defacement; 8=11-20% defacement; 7=21-30% defacement; 6=31-40% defacement; 5=41-50% defacement; 4=51-60% defacement; 3=61-70% defacement; 2=71-80% defacement; 1=81-90% defacement; and 0=91-100% defacement. A grid that divides the circular area into 20 equal sections as shown in FIG. 1 was used to estimate the extent (percent defacement) of fungal growth.

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

The invention claimed is:

1. A latex paint composition resistant to cellulose-supportable fungus growth, said composition inhibiting fungus growth upon a dried, painted cellulose substrate and upon the dried paint film, and comprises an aqueous vehicle having dispersed therein a film-forming binder and a pigment, and further containing a cellulose-supportable fungus growth-inhibiting amount of a benzoxaborole compound of Formula C, below,

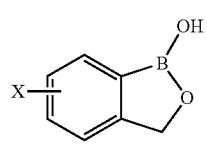

C where X is H, $C_1$-$C_7$ acyl, cyano, halogen, $C_1$-$C_6$ hydrocarbyl, carboxyl, $C_1$-$C_6$ hydrocarbyloxy carboxylate, carboxamido whose amido nitrogen atom is unsubstituted, monosubstituted with a $R^1C_1$-$C_6$ hydrocarbyl group, di-substituted with a $R^2$ $C_1$-$C_6$ hydrocarbyl group that is the same as or different from $R^1$, or the amido group nitrogen atom together with $R^1$ and $R^2$ form a 5- or 6-membered ring that can contain one additional hetroatom that is oxygen or nitrogen and wherein the additional nitrogen atom when present in that ring can be unsubstituted or substituted with one $C_1$-$C_6$ hydrocarbyl group.

2. The latex paint composition according to claim 1, wherein said benzoxaborole is a compound of, Formula C-1

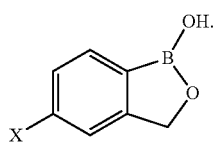

C-1

3. The latex paint composition according to claim 2, wherein X is other than H.

4. The latex paint composition according to claim 3, wherein said benzoxaborole is one or more of

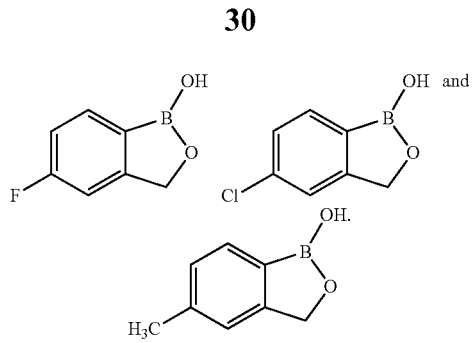

5. The latex paint composition according to claim 1, wherein said benzoxaborole is present in said latex paint composition in an amount of about 5 to about 2000 µg/mL.

6. The latex paint composition according to claim 1, wherein said cellulose-supportable fungus is selected from the group of genera consisting of one or more of *Alternaria, Aspergillus, Aureobasidium, Rhizopus, Mucor, Penicillium, Cladosporium, Epicoccum, Chaetomium, Acremonium, Ulocladium, Fusarium* and *Stachybotrys*.

7. A method of inhibiting the growth of a cellulose-supportable fungus on a cellulosic substrate free of visible fungus growth that comprises the step of coating said cellulosic substrate that is free of visible fungus growth with a latex paint of claim 1.

8. The method according to claim 7, wherein said cellulosic substrate is a paper-containing surface.

9. The method according to claim 8, wherein said paper-containing substrate is one or more, of those selected from the group consisting of plasterboard, a cellulosic ceiling tile, cardboard and wallpaper.

10. The method according to claim 7, wherein said paper-containing substrate has one or more previously applied and dried coats of paint.

11. The method according to claim 7, wherein said paper-containing substrate is free of previously applied and dried coats of paint.

12. The method according to claim 7, wherein said benzoxaborole is a compound of Formula C-1

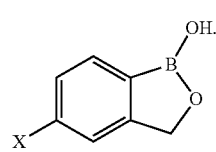

C-1

13. The method according to claim 7, wherein said benzoxaborole is one or more of

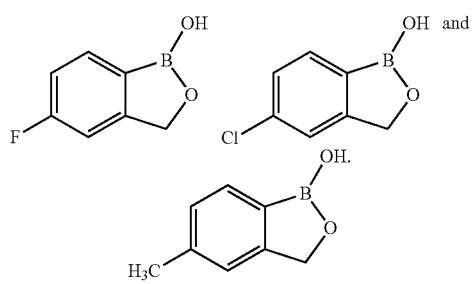

14. The method according to claim 7, wherein said benzoxaborole is present in said latex paint composition in an amount of about 5 to about 2000 µg/mL.

15. The method according to claim 7, wherein said cellulose-supportable fungus is selected from the group consisting of one or more of *Alternaria alternata, Aspergillus niger, Aureobasidium pullulans, Rhizopus* spp., *Mucor* spp., *Aspergillus fumigatus, Penicillium brevicompactum, Penicillium corylophilum, Penicillium purpurogenum, Penicillium chrysogenum, Cladosporium* spp., *Epicoccum* spp., *Chaetomium globosum, Acremonium* spp., *Ulocladium* spp., and *Fusarium oxysporum* and *Stachybotrys chartarum*.

16. A method of inhibiting the growth of a cellulose-supportable fungus on a cellulosic substrate that has a visible cellulose-supportable fungus infection that comprises overpainting said substrate with a latex paint of claim 1.

17. The method according to claim 16, wherein said cellulosic substrate is a paper-containing substrate.

18. The method according to claim 17, wherein said paper-containing substrate is one or more of those selected from the group consisting of plasterboard, a cellulosic ceiling tile, cardboard and wallpaper.

19. The method according to claim 17, wherein said paper-containing substrate has one or more previously applied and dried coats of paint.

20. The method according to claim 17, wherein said benzoxaborole is a compound of Formula C-1

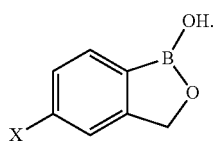

21. The method according to claim 20, wherein said benzoxaborole is one or more of

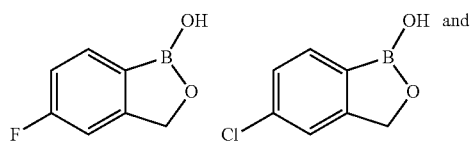

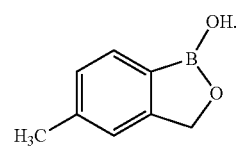

22. The method according to claim 17, wherein said benzoxaborole is present in said latex paint composition in an amount of about 5 to about 2000 µg/mL.

23. The method according to claim 17, wherein said cellulose-supportable fungus is selected from the group consisting of one or more of *Alternaria alternata, Aspergillus niger, Aureobasidium pullulans, Rhizopus* spp., *Mucor* spp., *Aspergillus fumigatus, Penicillium brevicompactum, Penicillium corylophilum, Penicillium purpurogenum, Penicillium chrysogenum, Cladosporium* spp., *Epicoccum* spp., *Chaetomium globosum, Acremonium* spp., *Ulocladium* spp., *Fusarium oxysporum* and *Stachybotrys chartarum*.

* * * * *